United States Patent
Malenfant et al.

(10) Patent No.: US 8,252,556 B2
(45) Date of Patent: *Aug. 28, 2012

(54) REVERSE CUMATE REPRESSOR MUTANT

(75) Inventors: Felix Malenfant, Sainte-Angele-de-Monnoir (CA); Alaka Mullick, Montreal West (CA)

(73) Assignee: National Research Council of Canada, Ottawa, Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/070,975

(22) Filed: Mar. 24, 2011

(65) Prior Publication Data

US 2011/0171686 A1    Jul. 14, 2011

Related U.S. Application Data

(60) Division of application No. 12/331,786, filed on Dec. 10, 2008, now Pat. No. 7,935,788, which is a continuation-in-part of application No. 11/575,621, filed on Nov. 19, 2007.

(51) Int. Cl.
| | |
|---|---|
| *C12P 21/06* | (2006.01) |
| *C12N 15/00* | (2006.01) |
| *C12N 5/02* | (2006.01) |
| *C12N 5/10* | (2006.01) |
| *C07H 21/00* | (2006.01) |
| *C07H 21/04* | (2006.01) |

(52) U.S. Cl. ....................................... 435/69.1
(58) Field of Classification Search ...................... None
See application file for complete search history.

(56) References Cited

FOREIGN PATENT DOCUMENTS
WO    WO 02/088346 A2 * 11/2002

OTHER PUBLICATIONS

Eaton, J. Bacteriol. 179:3171-3180, 1997.*
Even et al., J. Bacteriol. 188:2184-2197, 2006.*
Urlinger et al., PNAS 97:7963-7968, 2000.*
Mullick et al., BMC Biotechnol. 6:1-18, Nov. 2006.*
Choi et al., Microbiology 149:795-805, 2003.*

* cited by examiner

*Primary Examiner* — David J Steadman

(57) ABSTRACT

Recently, the development of inducible expression systems has involved exploitation of the p-cym operon from *Pseudomonas putida*. Disclosed herein are novel expression systems and components thereof, which involve the development of a CymR variant with reverse DNA binding activity, such that they exhibit increased affinity for DNA in a presence rather than an absence of an effector molecule such as cumene or an equivalent thereof. Also disclosed are the CymR variant, fusion proteins incorporating such a variant, and its use in the control and expression of polynucleotides. The CymR variant comprises a 142Glu to 142Gly single point mutation of wild type CymR.

16 Claims, 14 Drawing Sheets

Cumate(+)   Cumate(−)

Cumate(+)   Cumate (−)

SEQUENCE LISTING

<160> NUMBER OF SEQ ID NOS: 14

<210> SEQ ID NO 1
<211> LENGTH: 621
<212> TYPE: DNA
<213> ORGANISM: Pseudomonas putida
<220> FEATURE:
<221> NAME/KEY: CDS
<222> LOCATION: (1)..(621)

<400> SEQUENCE: 1

```
atg gtg atc atg agt cca aag aga aga aca cag gca gag cgc gca atg      48
Met Val Ile Met Ser Pro Lys Arg Arg Thr Gln Ala Glu Arg Ala Met
1               5                   10                  15 gag acc cag ggc aag ttg att gca gcg gcc ctg ggg gtt tta cgg gaa      96
Glu Thr Gln Gly Lys Leu Ile Ala Ala Ala Leu Gly Val Leu Arg Glu
            20                  25                  30 aaa ggt tac gcg gga ttc cgg atc gca gat gtg ccc ggt gct gca ggt     144
Lys Gly Tyr Ala Gly Phe Arg Ile Ala Asp Val Pro Gly Ala Ala Gly
        35                  40                  45 gtc tcg aga gga gcg cag agc cat cat ttc ccg aca aag ctt gag ctt     192
Val Ser Arg Gly Ala Gln Ser His His Phe Pro Thr Lys Leu Glu Leu
    50                  55                  60
```

-continued

```
ctg ctt gcc act ttt gaa tgg ctt tac gaa cag atc acc gaa cgc agt      240
Leu Leu Ala Thr Phe Glu Trp Leu Tyr Glu Gln Ile Thr Glu Arg Ser
65                  70                  75                  80 cgg gct cga tta gcg aaa ttg aag cca gag gat gac gtc atc cag caa      288
Arg Ala Arg Leu Ala Lys Leu Lys Pro Glu Asp Asp Val Ile Gln Gln
                85                  90                  95 atg ctg gac gac gcc gcc gaa ttt ttc ctc gac gat gac ttc tct atc      336
Met Leu Asp Asp Ala Ala Glu Phe Phe Leu Asp Asp Asp Phe Ser Ile
            100                 105                 110 agc ctt gat ttg att gtg gct gcc gac cgg gat cca gtg tta cgc gag      384
Ser Leu Asp Leu Ile Val Ala Ala Asp Arg Asp Pro Val Leu Arg Glu
        115                 120                 125 ggt att cag cgc acg gta gag agg aat cgg ttt gtc gtc ggg gat ata      432
Gly Ile Gln Arg Thr Val Glu Arg Asn Arg Phe Val Val Gly Asp Ile
    130                 135                 140 tgg ctt ggt gtt ctg gtg agc cgt ggt ctt tcg cgt gat gat gca gaa      480
Trp Leu Gly Val Leu Val Ser Arg Gly Leu Ser Arg Asp Asp Ala Glu
145                 150                 155                 160 gat atc ctt tgg ttg ata ttc aat tcg gtg cgt ggg ctt gct gtt cgt      528
Asp Ile Leu Trp Leu Ile Phe Asn Ser Val Arg Gly Leu Ala Val Arg
                165                 170                 175 agc cta tgg cag aag gac aaa gaa cgc ttt gag cgt gtc agg aac tcg      576
Ser Leu Trp Gln Lys Asp Lys Glu Arg Phe Glu Arg Val Arg Asn Ser
            180                 185                 190 aca ctc gaa att gcg cga gag cgg tac gcg aaa ttc aag cgc tag          621
Thr Leu Glu Ile Ala Arg Glu Arg Tyr Ala Lys Phe Lys Arg
        195                 200                 205
```

<210> SEQ ID NO 2
<211> LENGTH: 206
<212> TYPE: PRT
<213> ORGANISM: Pseudomonas putida

<400> SEQUENCE: 2

```
Met Val Ile Met Ser Pro Lys Arg Arg Thr Gln Ala Glu Arg Ala Met
1               5                   10                  15

Glu Thr Gln Gly Lys Leu Ile Ala Ala Leu Gly Val Leu Arg Glu
            20                  25                  30

Lys Gly Tyr Ala Gly Phe Arg Ile Ala Asp Val Pro Gly Ala Ala Gly
        35                  40                  45

Val Ser Arg Gly Ala Gln Ser His His Phe Pro Thr Lys Leu Glu Leu
    50                  55                  60

Leu Leu Ala Thr Phe Glu Trp Leu Tyr Glu Gln Ile Thr Glu Arg Ser
65                  70                  75                  80

Arg Ala Arg Leu Ala Lys Leu Lys Pro Glu Asp Asp Val Ile Gln Gln
                85                  90                  95

Met Leu Asp Asp Ala Ala Glu Phe Phe Leu Asp Asp Asp Phe Ser Ile
            100                 105                 110

Ser Leu Asp Leu Ile Val Ala Ala Asp Arg Asp Pro Val Leu Arg Glu
        115                 120                 125

Gly Ile Gln Arg Thr Val Glu Arg Asn Arg Phe Val Val Gly Asp Ile
    130                 135                 140

Trp Leu Gly Val Leu Val Ser Arg Gly Leu Ser Arg Asp Asp Ala Glu
145                 150                 155                 160

Asp Ile Leu Trp Leu Ile Phe Asn Ser Val Arg Gly Leu Ala Val Arg
                165                 170                 175

Ser Leu Trp Gln Lys Asp Lys Glu Arg Phe Glu Arg Val Arg Asn Ser
            180                 185                 190
```

Thr Leu Glu Ile Ala Arg Glu Arg Tyr Ala Lys Phe Lys Arg
     195                 200                 205

<210> SEQ ID NO 3
<211> LENGTH: 20
<212> TYPE: DNA
<213> ORGANISM: Artificial sequence
<220> FEATURE:
<223> OTHER INFORMATION: Chemically synthesized

<400> SEQUENCE: 3
tccactttgc ctttctctcc                                              20

<210> SEQ ID NO 4
<211> LENGTH: 26
<212> TYPE: DNA
<213> ORGANISM: Artificial sequence
<220> FEATURE:
<223> OTHER INFORMATION: Chemically synthesized

<400> SEQUENCE: 4 gttttcgta cgcgcgcggc tgtacg                                        26

<210> SEQ ID NO 5
<211> LENGTH: 23
<212> TYPE: DNA
<213> ORGANISM: Artificial sequence
<220> FEATURE:
<223> OTHER INFORMATION: primer rev-2-wild-F

<400> SEQUENCE: 5
gtcgtcgagg atatatggct tgg                                          23

<210> SEQ ID NO 6
<211> LENGTH: 23
<212> TYPE: DNA
<213> ORGANISM: Artificial sequence
<220> FEATURE:
<223> OTHER INFORMATION: primer rev-2-wild-R

<400> SEQUENCE: 6
ccaagccata tatcctcgac gac                                          23

<210> SEQ ID NO 7
<211> LENGTH: 22
<212> TYPE: DNA
<213> ORGANISM: Artificial sequence
<220> FEATURE:
<223> OTHER INFORMATION: primer rev-1-wild-F

<400> SEQUENCE: 7
gggatccagc gttacgcgag gg                                           22

<210> SEQ ID NO 8
<211> LENGTH: 22
<212> TYPE: DNA
<213> ORGANISM: Artificial sequence
<220> FEATURE:
<223> OTHER INFORMATION: primer rev-1-wild-R

<400> SEQUENCE: 8
ccctcgcgta acgctggatc cc                                           22

<210> SEQ ID NO 9
<211> LENGTH: 25
<212> TYPE: DNA

```
<213> ORGANISM: Artificial sequence
<220> FEATURE:
<223> OTHER INFORMATION: primer MutagR

<400> SEQUENCE: 9 gttttctcgta cgcgcgcggc tgtac                                            25

<210> SEQ ID NO 10
<211> LENGTH: 20
<212> TYPE: DNA
<213> ORGANISM: Artificial sequence
<220> FEATURE:
<223> OTHER INFORMATION: primer S-Ecoli

<400> SEQUENCE: 10
tccactttgc ctttctctcc                                                   20

<210> SEQ ID NO 11
<211> LENGTH: 34
<212> TYPE: DNA
<213> ORGANISM: Artificial sequence
<220> FEATURE:
<223> OTHER INFORMATION: primer mut2,3 corrected R

<400> SEQUENCE: 11
agaacaccaa gccacatatc ctcgacgaca aacc                                   34

<210> SEQ ID NO 12
<211> LENGTH: 33
<212> TYPE: DNA
<213> ORGANISM: Artificial sequence
<220> FEATURE:
<223> OTHER INFORMATION: primer mut2,3 corrected F

<400> SEQUENCE: 12
ggtttgtcgt cgaggatatg tggcttggtg ttc                                    33

<210> SEQ ID NO 13
<211> LENGTH: 18
<212> TYPE: DNA
<213> ORGANISM: Artificial sequence
<220> FEATURE:
<223> OTHER INFORMATION: primer MutagN

<400> SEQUENCE: 13
ggggagaaag gacaggcg                                                     18

<210> SEQ ID NO 14
<211> LENGTH: 18
<212> TYPE: DNA
<213> ORGANISM: Artificial sequence
<220> FEATURE:
<223> OTHER INFORMATION: primer CR5atgseqF

<400> SEQUENCE: 14
gatctggcca tacacttg                                                     18
```

US 8,252,556 B2

REVERSE CUMATE REPRESSOR MUTANT

CROSS-REFERENCE TO RELATED APPLICATIONS

This application is a divisional of co-pending U.S. application Ser. No. 12/331,786, filed Dec. 10, 2008, which is a continuation-in-part of U.S. application Ser. No. 11/575,621 filed Nov. 19, 2007 which is a national entry under 35 USC §371 of International application PCT/CA05/01508 filed Oct. 3, 2005 claiming the benefit of U.S. provisional application 60/614,992 filed Oct. 4, 2004, the entire contents of all of which are herein incorporated by reference.

TECHNICAL FIELD

The present invention relates to the field of gene expression, and in particular systems for the inducible expression of a DNA sequence, particularly an exogenous DNA sequence.

BACKGROUND ART

Techniques in molecular and cellular biology often involve the introduction of an exogenous genetic sequence into a cell, for example encoding an open reading frame, and the expression of the exogenous sequence within the cell to generate the encoded peptide or protein. Typically, the open reading frame is incorporated into a suitable vector under the control of a promoter sequence and promoter elements suitable for the binding of appropriate transcription factors and RNA polymerase. In the way, the vector utilizes the expression machinery of the host cell to co-ordinate expression.

Such expression systems may be broadly divided into those that involve constitutive expression wherein the degree of expression cannot be controlled, and those that enable inducible expression wherein the degree of expression can be controlled by external factors. Inducible expression systems are particularly useful where it is desirable to carefully control expression of a foreign protein in a host cell, for example to simulate a normal, endogenous expression profile. In other circumstances, inducible expression may allow the study of proteins whose constitutive expression might not be tolerated by the host cell. In some circumstances, the only way to generate a cell line or a recombinant viral vector that expresses this protein, is to use an inducible system, which is maintained in the off state at most times, such that expression is turned on to a desired level, or for a desired period, only at the time of the experiment.

Some expression systems of the prior art are derived from prokaryotes, and of these two have proved particularly useful: namely the lac and the tet operons. More recently, another inducible system has been developed as disclosed in United States patent publication 2004/0205834 published Oct. 14, 2004, corresponding to U.S. application Ser. No. 10/135,362, filed 31 May 2002, which is incorporated herein by reference. In preferred embodiments, this system is suitable for use in mammalian cells for a range of applications including those that require tight control or the need high-level expression. This new gene-switch is similar to the widely used Tet-system[1], but it makes use of a different bacterial repressor derived from the *Pseudomonas putida* F1 p-cymene operon. In *P. putida*, the degradative pathway for p-cymene to its benzoate derivative p-cumate consists of 6 genes organized in an operon (cym). The cym operon is followed by the cmt operon that is responsible for the further degradation of cumate. The expression of the genes in both operons is regulated by a repressor protein molecule (CymR) of about 28 kD that binds operator sequences downstream of the start site of the promoter[2]. CymR is in a DNA-binding configuration only in the absence of cymene or cumate, the effector molecule[3,4,B].

United States patent publication 2004/0205834 discloses the transformation of CymR into an activator (cTA) by fusion to a VP16 activation domain. In the context of adenoviral vectors, relatively low amounts of AdCMVcTA are required to achieve high expression levels from the Cumate-regulated promoter CR5. This contrasts to the Tet-switch where large amounts of reporter and activator virus (AdCMVtTA) are required to achieve the same levels of activation. Furthermore, the CR5/cTA system performs better than the strong promoter CMV5 in all cell lines tested. Thus, cell lines stably expressing cTA are useful for achieving maximal protein expression. Since maximal protein production is presumably incompatible with maximal cell growth, the ability to down-regulate protein production in cTA cells in the presence of cumate during clone selection facilitates the selection of high producing clones. However, in its current configuration, this system is not as readily amenable to large-scale production since the induction of protein secretion requires the removal of cumate, a process that is cumbersome in large-scale culture.

There remains a continuing need for inducible expressions system that permit tight regulation of expression of associated exogenous sequences. In particular, there is an increasing need for inducible expression systems that permit regulation of the level and/or duration of expression. Ideally, such expression systems may permit near total silencing of gene expression as desired.

DISCLOSURE OF THE INVENTION

It is an object of the invention, at least in preferred embodiments, to provide an inducible expression system.

It is another object of the present invention, at least in preferred embodiments, to provide an inducible expression system in which a level and/or duration of expression can be regulated.

In one aspect of the invention there is provided an isolated polypeptide comprising a sequence variant of CymR that exhibits a higher affinity for a CymR response element when in a presence rather than an absence of an effector molecule. In preferred embodiments the polypeptide further comprises a transactivation domain covalently attached to the sequence variant of CymR.

In another aspect the invention provides for an isolated polynucleotide encoding the polypeptide of the invention.

In another aspect the invention provides a construct comprising the isolated polynucleotide of the invention in operable association with a promoter sequence suitable for causing expression of said polynucleotide to generate said polypeptide when said construct is transformed into a host cell.

In another aspect the invention provides a eukaryotic host cell transformed with the construct of the invention.

Preferably, the host cell is further transformed with a second construct comprising:

(i) a promoter;
(ii) at least one CymR response element; and
(iii) an open reading frame encoding a protein to be expressed, in operable association with said promoter and said at least one CymR response element, whereby in an absence of an effector molecule said CymR variant exhibits reducing binding to said at least one CymR response element to cause little or no expression of said open reading frame, and in a presence of an effector molecule said CymR variant exhibits increased binding to said at least one CymR response element to cause expression of said open reading frame, thereby to generate said protein.

In another aspect the invention provides for a method for producing a recombinant protein in the host cell of the invention, the method comprising the steps of:
(a) transforming the host cell with a second construct comprising:
  (i) a promoter sequence;
  (ii) at least one CymR response element; and
  (iii) an open reading frame encoding said recombinant protein in operable association with said eukaryotic promoter and said at least one CymR response element;
(b) introducing an effector molecule that regulates CymR-mediated expression into the transformed cells of step (a) to induce the expression of said open reading frame thereby to generate said recombinant protein.

Preferably, the construct comprises in operable association with said isolated polynucleotide, at least one CymR response element, whereby expression of said polynucleotide in a host cell to generate said polypeptide can be regulated at least in part through binding of CymR to said response element. Preferably, the host cell is further transformed with an expression cassette expressing CymR, whereby in an absence of said effector molecule said CymR expressed from said expression cassette binds to said construct and inhibits expression of rcTA from said construct, and optionally binds to said second construct and inhibits expression of said open reading frame encoding said recombinant protein, and in a presence of said effector molecule said effector molecule inhibiting binding of said CymR to said construct to cause expression of rcTA, said rcTA binding said CymR response elements in said second construct to facilitate transactivation of said open reading frame causing expression of said recombinant protein.

In another aspect the invention provides for a method for regulating transcription of an open reading frame in operable association with a promoter and at least one CymR response element, the method comprising the steps of:
(a) providing a polypeptide comprising a CymR variant exhibiting reversed DNA binding capability in that the CymR variant exhibits stronger DNA binding activity in the presence rather than the absence of an effector molecule such as cumate or an equivalent thereof; and
(b) altering a concentration of said effector molecule.

In another aspect the invention provides for a kit for generating a eukaryotic cell comprising an exogenous gene selectively upregulatable in response to a presence of an effector molecule, the kit comprising;
(a) a first polynucleotide comprising:
  (i) a first promoter;
  (ii) at least one CymR response element; and
  (ii) a cloning site for an open reading frame positioned such that said open reading frame once positioned at said cloning site is in operable association with said promoter, and said at least one CymR response element;
(b) a second polynucleotide comprising;
  (i) a second promoter;
  (ii) an open reading frame encoding a rcTA in operable association with said promoter;
whereby each of said first and second polynucleotides are suitable for being transformed into a eukaryotic host cell, and in an absence of an effector molecule, said rcTA exhibiting reducing binding to said at least one CymR response element to cause little or no expression of said open reading frame, and in a presence of an effector molecule said CymR variant exhibiting increased binding to said at least one CymR response element to cause expression of said open reading frame.

Preferably, the kit further comprises:
(c) a third polynucleotide comprising:
  (i) a third promoter; and
  (ii) a second open reading frame encoding CymR or an equivalent thereof;
whereby in an absence of said effector molecule said CymR expressed from said third polynucleotide binds to said at least one CymR response element in said second polynucleotide to inhibit expression of rcTA therefrom, and optionally binds to said first polynucleotide to inhibit expression of said open reading frame, and in a presence of said effector molecule, said effector molecule inhibiting binding of said CymR to said at least one CymR response element in said second polynucleotide thereby to cause expression of rcTA, said rcTA binding said at least one CymR response element in said first polynucleotide thereby to facilitate expression of said open reading frame.

In another aspect the invention provides for a biological material derived from a deposit filed on Sep. 16, 2005 at the Canadian International Depository Authority in at the National Microbiology Laboratory, Health Canada, 1015 Arlington Street, Winnipeg, MB, Canada R3E 3R2, said deposit having an accession number selected from: 160905-01, 160905-02, and 160905-03. The invention further provides for a product derived from the biological material of the deposits mentioned above.

Certain exemplary embodiments provide for an isolated polypeptide comprising a sequence variant of CymR that exhibits a higher affinity for a CymR response element when in a presence rather than an absence of an effector molecule, the variant comprising a 142Gly mutation compared to wild-type CymR sequence.

Definitions

Figure 1:
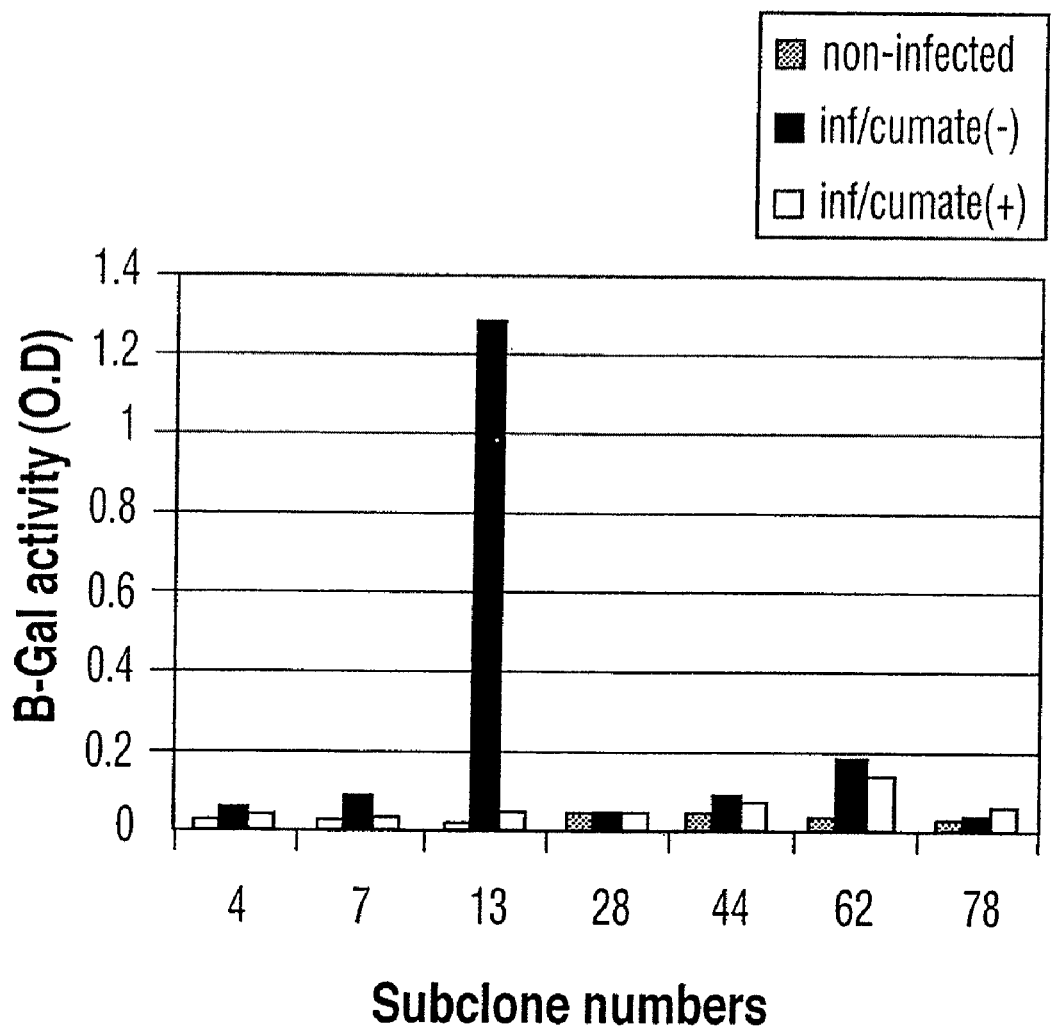
FIG. 1: Induction characteristics of various 293A-CR5-LacZ subclones. $1\times10^6$ 293A cells were transfected with 4 ug of linearized plasmid DNA pAdCR5LacZ-neo and 8 ul of PEI reagent, and selected under the presence of G418 (600-800 ug/ml) with the diluted ratio of 1-1.3 cell/well in 96-well plates. Resistant clones were picked up after 3 week cultivation, and verified by measurement of reporter β-Gal activity upon infection with adenovirus containing the fusion transactivator CymR-VP16 in the presence or absence of 200 ug/ml of cumate. The figure shows the subclone #13 displays the high activity of transactivator cTA and a good inhibition ratio, almost a 40-fold difference.

For the purpose of the present invention the description that follows uses a number of terms that refer to recombinant DNA technology. In order to provide a clear and consistent understanding of the specification and claims, including the scope given to such terms, the following definitions are provided.

Construct: refers to any recombinant polynucleotide comprising a vector and an open reading frame to be expressed as required under the control of a promoter. For example, a construct may comprise 'naked' DNA such as a plasmid, or may take the form of recombinant DNA encapsulated within a viral particle. Typically, a construct is designed for insertion of the recombinant polynucleotide into a host cell.

CymR response element: refers to any DNA or polynucleotide that is able to bind CymR and/or a mutant variant of CymR. Preferably, the capacity of the polynucleotide to bind CymR or a mutant variant of CymR is dependent upon a level of an effector molecule such as cumate or an equivalent thereof. Most preferably, the CymR response element is CuO.

Effector molecule: includes any molecule able to influence the DNA binding capacity of CymR or a variant thereof. Such effector molecules include cumate or an equivalent thereof. Such equivalents to cumate include, but are not limited to, Di-methyl p-aminobenzoic acid (DM PABA), trimethyl cumate, and ethylbenzoate, or a salt thereof, mainly para- or 4-substituted benzoate consisting of a bulky group of heteroatom, such a those selected from the group consisting of 3,4-dimethylbenzoate, 4-ethylbenzoate, 4-t-butylbenzoate, 4-phenylbenzoate, 4-benzylbenzoate, 4-ethoxybenzoate, 4-propyloxybenzoate, 4-n-butyloxybenzoate, 4-chlorobenzoate, 4-bromobenzoate, 4-iodobenzoate, 4-bromomethylbenzoate, 3,4-dichlorobenzoate, 4-trifluoromethylbenzoate, 4-ethyl-m-xylene, 4-vinyltoluene, 4-n-propyltoluene, 4-allytoluene, 4-fluoro-p-toluate, 3-chloro-p-toluate, and 4-bromo-m-toluate, an analogue of cumate such as Benzoic acid, p-methylbenzoic acid, p-ethylbenzoic acid, p-Propylbenzoic acid, cumic acid, p-isobutylbenzoic acid, p-tert-butylbenzoic acid, ibuprofen, p-aminobenzoic acid, p-N-methylaminobenzoic acid, p-N-dimethylaminobenzoic acid, p-N-methyl-N-ethylaminobenzoic acid and p-N-ethylaminobenzoic acid.

Expression vector: This and comparable terms refer to a vector which is capable of inducing the expression of DNA that has been cloned into it after transformation into a host cell. The cloned DNA is usually placed under the control of (i.e., operably linked to) certain regulatory sequences such a promoters or enhancers. Promoters sequences maybe constitutive, inducible or repressible.

Gene: As used herein, "gene" refers to any nucleic acid sequence that undergoes transcription as the result of promoter activity. A gene may encode an open reading frame of a particular protein, part thereof, or a particular peptide or polypeptide or, alternatively, may encode an RNA sequence that is of interest in itself, e.g. because it acts as an antisense inhibitor.

Host: Any prokaryotic or eukaryotic cell that is the recipient of a vector is the host for that vector. The term encompasses prokaryotic or eukaryotic cells that have been engineered to incorporated a gene in their genome. Cells that can serve as hosts are well known in the art as are techniques for cellular transformation (see e.g., Sambrook, et al., Molecular Cloning: A Laboratory Manual, 2nd ed., Cold Spring Harbor (1989)).

Operably linked: The term "operably linked" or "in operable association with" refers to genetic elements that are joined in such a manner that enables them to carry out their normal functions. For example, a gene is operably linked to a promoter when its transcription is under the control of the promoter and such transcription produces the protein normally encoded by the gene.

Recombinant: As used herein, the term "recombinant" refers to nucleic acid that is formed by experimentally recombining nucleic acid sequences and sequence elements. A recombinant host would be any host receiving a recombinant nucleic acid and the term "recombinant protein" refers to protein produced by such a host.

Substantially pure or purified: As used herein, "substantially pure" or "purified" means that the desired product is free or at least essentially free from contaminating cellular components. Contaminants may include, but are not limited to, proteins, carbohydrates and lipids. One method for determining the purity of a protein or nucleic acid is by electrophoresis in a matrix such as polyacrylamide or agarose. Purity is evidence by the appearance of a single band after staining.

Viral vector: As used herein, "viral vector" and equivalent terms refer to viruses that are utilized for transferring selected DNA or RNA sequences into a host cell. The vectors maybe utilized for the purpose of transferring DNA into cells either in vitro or in vivo. Viruses that have been commonly used for the latter purpose include the retroviruses, adenoviruses, parvoviruses and herpes viruses.

Preferably/preferred: refers to preferred features or aspects of the broadest embodiments of the invention, unless stated otherwise.

Promotor: A DNA sequence that initiates the transcription of a gene. Promoters are typically found 5' to the gene and located proximal to the start codon. If a promoter is of the inducible type, then the rate of transcription increases in response to an inducing agent. Expression: Expression is the process by which a polypeptide is produced from DNA. The process involves the transcription of the gene into mRNA and the translation of this mRNA into a polypeptide. Depending on the context in which used, "expression" may refer to the production of RNA, protein or both.

Transactivation domain: refers to any peptide, protein or part thereof capable of some form of interaction with transcription factors and/or and RNA polymerase to facilitate transactivation of a promoter and expression of a section of DNA operably linked thereto. For example, in selected embodiments the polypeptides of the invention may include fusion proteins comprising a CymR variant, or part thereof, covalently attached to a transactivation domain. In such embodiments, the CymR variant may provide selective DNA binding activity, and when required the attached transactivation domain may provide transactivation activity. Any transactivation domain or part thereof may be used in accordance with the polypeptides of the present invention. For example, such transactivation domains may be selected from the following non-limiting group: VP-16, TAF-1, TAF-2, TAU-1, TAU-2, SH2, and B42 acidic activator transactivation domain. However, persons of skill in the art will appreciate that many other transactivation domains would achieve desirable results in accordance with the teachings of the invention.

DETAILED DESCRIPTION OF THE PREFERRED EMBODIMENTS

To address the increasing demands from both basic researchers and industry, the development of regulatory gene expression systems has made progress in the past 20 years. Several inducible gene switch systems have been reported in the last few years (12-18). The invention disclosed herein provides, at least in preferred embodiments, for a novel inducible gene expression system based on the cumate gene switch system (19). This previous system displayed high-level activity in mammalian cells compared with the Tet-inducible system, a widely used tool for the studies of gene function. However, despite these attractive properties, the cumate system has limitations for certain applications. A major drawback is the need to remove cumate (the inducer) to induce gene expression, since this is cumbersome for large-scale cultivation. As an alternative, the inventors have developed a modified cumate-dependent gene switch or rcTA gene switch, wherein cumate addition, rather than removal, is required to activate gene expression. The modified activator, rcTA, in preferred embodiments continues to display the desirable strong activation potential of the cTA in that for example, rcTA-activated CR5 promoter can display remarkably high level transgene expression in mammalian cells in transient or stable expression systems.

The inventors utilized mutagenesis techniques as an approach for generation of rcTA gene switch. In general, the DNA binding domain of an inducible system plays an important role in recognizing and binding to the unique regulatory DNA sequence. With proprietary technology of a positive selection system (20), the inventors were able to establish adenovirus libraries for the screening of CymR mutants generated by PCR random mutagenesis. CymR is a 28 kDa protein encoded by a 600-bp gene. Without detailed information regarding the structure of CymR, the inventors undertook a random mutagenesis approach. Three libraries of CymR were established with mutation frequencies ranging from 0-3 to 7-13 per kb to increase the chances of finding the appropriate mutants. The experimental protocol used to generate the library with the highest mutation frequency (7-13 per kb) gave rise to a wide spectrum of mutation frequencies, from low to high. Thus, interesting mutants were picked from this library, each with a different activity in responsive to cumate induction.

The previously developed cumate gene switch system demonstrated that the artificial transactivator cTA has a higher intrinsic activation potential than tTA, the transactivator that activates the tetracycline-responsive promoter (19). The new rcTA transactivator, at least in preferred embodiments, maintained an intrinsic activation potential comparable to cTA. In particularly preferred embodiments the inventors improve the performance of this system even further, by incorporating one or more additional regulatory elements (e.g. CuO, the CymR binding site), downstream of a promoter such as CMV5 promoter and upstream of an open reading frame for rcTA. The goal for this design was to very tightly control the expression of the open reading frame for rcTA, since CymR binding is capable of suppressing promoter activity (19). In the absence of cumate, CymR protein binds to the CuO element to inhibit rcTA expression. As a result, the promoter CR5 is not activated, and the transgene under its control is not transcribed. With the cumate induction, however, the repressor CymR is released, and rcTA is then expressed and binds to the CuO repeats upstream of the minimal CMV promoter in the CR5 promoter (19). The activated CR5 promoter initiates transcription of the gene of interest. The results described herein show that the tight control of the rcTA expression indeed contributes to reduce the background in these preferred systems.

It is reported that, today about 60-70% of all of recombinant protein pharmaceuticals are produced in mammalian cells, and most of them are mainly expressed in immortalized Chinese hamster ovary cells (CHO). It is not only because this cell line has gained regulatory approval, but also because this cell line possesses some properties that make it attractive for the bio-pharmaceutical industry, such as rapid growth, and ease of adaptation to serum-free growth. In addition, progress has been made to regulate transgene expression in CHO cells with both tetracycline- and streptogramin-based gene regulation systems (21). Compared to cTA, the single or double regulated rcTA avoids the step of cumate removal, a cumbersome activity for the large-scale protein production. Therefore, the invention encompasses, at least in preferred embodiments, a stable CHO cell line by co-transfection of the plasmids pAdCMV5CuOrcTA and pAdCMV5-CymR into CHO cells. One CHO-CymR/rcTA clone (see Examples) displayed particularly strong promoter activity in the ON state and tight control of gene expression in the OFF state.

The present invention therefore provides, at least in preferred embodiments, a powerful gene switch system that may be suitable for use in many applications from the production of recombinant proteins on an industrial scale, to the fine tuning of heterologous gene expression for academic research purposes. Moreover, the inventors have succeeded in the development of an expression system that, at least in preferred embodiments, permits the induction of expression of an exogenous sequence in a eukaryotic host cell in response to the addition, rather than the withdrawal, of an effector molecule such as cumate (or an equivalent thereof) from a culture media. In this way, protein expression (and optionally secretion) may be activated in eukaryotic host cells through the expression system without the need to withdraw cumate from the culture media. The expression systems of the invention provide greater flexibility in selected applications than the expression systems of the prior art involving cumate withdrawal for expression activation. In preferred embodiments, the expression system of the invention permits a high level of expression when desired upon addition of cumate, and yet the expression is virtually eliminated upon removal of cumate. In other preferred embodiments, the expression system of the invention permits inducible expression for a desired level and/or period.

Although specific mutant variants of CymR are described herein, it should be noted that the invention is not limited in this regard, and encompasses any CymR-derived polypeptide that exhibits a reverse DNA binding capacity such that it exhibits a higher affinity for a suitable DNA response element in the presence, rather than the absence of cumate. Such mutant variants include those that exhibit slightly increased DNA binding activity in the presence of cumate, and slightly reduced DNA binding in the absence of cumate. In selected embodiments, the invention encompasses CymR variants that exhibit the aforementioned reverse DNA binding capacity, as well as fusion proteins comprising such CymR variants fused to a domain suitable for facilitating transactivation once the CymR variant binds a suitable DNA response element within or near a promoter. Any transactivation domain may be used in accordance with the polypeptides of the invention, including but not limited to a VP-16 domain. A person of skill in the art will appreciate that any transactivation domain may be utilized in order to achieve an rcTA of the present invention. Such a transactivation domain may be derived, for example, from any known transcription factor, and may be specifically designed for the intended host cell or tissue type towards which expression using the rcTA is directed.

The teachings regarding mutagenesis techniques that form part of this specification, or any other mutagenesis techniques that are well known in the art, may be utilised to generate CymR variants with or without fused transactivation domains that exhibit similar or equivalent reverse DNA binding activity compared to the wild-type CymR protein. The generation of such mutant variants, and the testing of such mutant variants, is enabled either through the teachings presented herein, and also through other mutagenesis systems and kits as available for example from companies such as Biorad and Promega.

For this reason, the CymR variants of the present invention include any CymR variant that exhibits reverse DNA binding activity, including but not limited to:
  (i) the polypeptide with the sequence CymR 142Gly;
  (ii) a polypeptide with the sequence of SEQ ID NO: 2;
  (iii) a polypeptide comprising at least a part of SEQ ID NO: 2 that exhibits a higher affinity for CuO or any other CymR response element, in a presence rather than an absence of an effector molecule such as cumate or an equivalent thereof; or
  (iv) a polypeptide having at least 70% identity to the polypeptide of SEQ ID NO: 2 that exhibits a higher affinity for CuO or any other CymR response element in a presence rather than an absence of an effector molecule such as cumate or an equivalent thereof. In preferred embodiments, the CymR variant has at least 80% identity to SEQ ID NO: 2. In further preferred embodiments, the CymR variant has at least 90% identity to SEQ ID NO: 2. In further preferred embodiments, the CymR variant has at least 95% identity to SEQ ID NO: 2. In most preferred embodiments, the CymR variant has at least 99% identity to SEQ ID NO: 2.

In this way, the CymR variants and fusion proteins of the invention include those with amino acid substitutions, deletions and insertions compared to wild-type CymR shown for example in SEQ ID NO: 2.

The invention further encompasses any system for the expression of a heterologous gene in a host cell that involves the use of a CymR variant with a reverse DNA binding capacity. Such systems enable, at least in preferred embodiments, the selective induction of expression of the gene in the presence rather than the absence of cumate.

As described herein, the inventors utilized proprietary technology involving positive selection to generate an adenoviral library of CymR mutants (this proprietary technology is described for example, in U.S. Pat. No. 6,620,618 issued Sep. 16, 2003, and U.S. Pat. No. 6,642,052 issued Nov. 4, 2003, the disclosures of which are incorporated herein by reference). The library was successfully screened for CymR mutants with reversed DNA binding properties, as described in the examples.

In other embodiments, the present invention also encompasses various eukaryotic host cells comprising the plasmids, constructs and vectors of the invention. For example, the invention encompasses, at least in preferred embodiments, a host cell comprising a construct comprising an open reading frame encoding a CymR variant or rcTA of the invention under the control of a suitable promoter. Further, the host cell may comprise a second construct comprising: (i) a promoter; (ii) at least one CymR response element; and (iii) an open reading frame encoding a protein to be expressed, in operable association with said eukaryotic promoter and said at least one CymR response element, whereby in an absence of an effector molecule such as cumate or an equivalent thereof, said CymR variant exhibiting reducing binding to said at least one CymR response element to cause little or no expression of said open reading frame, and in a presence of an effector molecule said CymR variant exhibiting increased binding to said at least one CymR response element to cause expression of said open reading frame, thereby to generate said protein.

Other embodiments of the invention include methods for producing a recombinant protein in the host cell of the invention, the method comprising the steps of:
  (a) transforming the host cell with a construct comprising:
    (i) a promoter sequence;
    (ii) at least one CymR response element; and
    (iii) an open reading frame encoding said recombinant protein in operable association with said eukaryotic promoter and said at least one CymR response element;
  (b) introducing an effector molecule that regulates CymR-mediated expression into the transformed cells of step (a) to induce the expression of said gene and generate said recombinant protein.

Each promoter may be selected from any suitable promoter such as for example the CMV, VIP, tk, HSP, MLP, and MMTV promoters.

In other embodiments of the invention, there is provided a method for regulating transcription of an open reading frame in operable association with a promoter and at least one CymR response element, the method comprising the steps of:
  (a) providing a polypeptide comprising a CymR variant exhibiting reversed DNA binding capability in that the CymR variant exhibits stronger DNA binding activity in the presence rather than the absence of an effector molecule such as cumate or an equivalent thereof; and
  (b) altering a concentration of said effector molecule.

The invention also provides for systems and kits, for example for generating a eukaryotic cell comprising an exogenous gene selectively upregulatable in response to a presence of an effector molecule such as cumate or an equivalent thereof. For example, such a kit may at least comprise;
  (a) a first polynucleotide comprising:
    (i) a first promoter;
    (ii) at least one CymR response element; and
    (ii) a cloning site for an open reading frame positioned such that said open reading frame once positioned at said cloning site is in operable association with said promoter, and said at least one CymR response element;
  (b) a second polynucleotide comprising;
    (i) a second promoter;
    (ii) an open reading frame encoding a rcTA in operable association with said promoter;
  whereby each of said first and second polynucleotides are suitable for being transformed into a eukaryotic host cell, and in an absence of an effector molecule such as cumate or an equivalent thereof, said rcTA exhibiting reducing binding to said at least one CymR response element to cause little or no expression of said open reading frame, and in a presence of an effector molecule said CymR variant exhibiting increased binding to said at least one CymR response element to cause expression of said open reading frame.

Selected embodiments of the invention will be further described below with reference to numbered examples, which are in no way intended to limit the scope and breadth of the invention as encompassed by the appended claims.

EXAMPLES

Example 1

Generation of a Stable 293A Cell Line with a Reporter Gene LacZ and a Chimeric Promoter CR5

$1\times10^6$ 293A cells were plated in a 60 mm dish with fresh DMEM supplemented with 5% FBS and 1% L-Glutamine one day prior to the transfection. 4 ug of linearized plasmid DNA pAdCR5LacZ-neo (Mullick et al 2001) was transfected into 293A cells using 8 ul of PEI reagent (obtained from Biotechnology Research Institute, Montreal). After 48 h transfection, the cells were transferred into 96-well plate with the diluted ratio of 1-1.3 cells per well. 600-800 ug/ml G418 was added to the culture medium for stable cell selection.

Resistant clones were picked after 3 weeks and verified by measurement of the expression of LacZ enzyme through the infection of adenovirus containing the fusion transactivator CymR-VP16[2].

Example 2

PCR Random Mutagenesis of CymR

A chemically synthesized double-stranded oligonucleotide, encoding a 5 Glycine peptide and bearing the sequences of a Not I restriction site at the 3' end and one mismatched Not I site at the 5' end, was ligated to equally restricted pAdCMV5cTA, which expressed the fusion transactivator, to generate a linker between CymR and VP16.

The PCR random mutagenesis of CymR was carried out using GeneMorph™ PCR Mutagenesis Kit (Stratagene, La Jolla, Calif.) according to the manufacturer's instructions. Briefly, the resulting plasmid pAdCMV5cTA-linker (referred to as cTA) was used as a template for CymR mutations and the PCR was performed with the primers 5'-TCCACTTTGC-CTTTCTCTCC(N terminus) (SEQ ID NO: 3) and 5'-GTTTTTCGTACGCGCGCGGCTGTACG (C terminus) (SEQ ID NO: 4) under conditions which would lead to frequent misincorporation of nucleotides. A total of three groups with different degrees of nucleotide misincorporation ranging from 0-3 mismatches per kb to 7-13 mismatches/kb were generated. All three groups were digested with BglII and NotI and ligated to Not I restricted pAd-PS-CMVcTA-IRES-GFP to substitute the wild-type CymR for the mutagenized ones. In order to optimize the diversity of the CymR mutations, electrophoratic transformation with *E. coli* DH 5α was carried out and maxi prepared DNA was ready for further application.

Example 3

Adenovirus Screening Assay

The adenovirus positive selection system has been described previously[4]. 293A cells were plated in 100 mm dish one day before the infection which was performed using modified adenovirus Ad5-ΔPS at a MOI of $10^{-2}$. 5 h later, 10 ug DNA of linearized pAd-PS-CMV-mut-cTA-IRES-GFP plasmid and 20 ul of PEI were transfected into the 100 mm dish of infected 293A cells to generate recombinant Ad5-PS-CMV-mut-cTA-IRES-GFP libraries. 3 days later, cells were harvested and frozen/thawed for 3 times to release the recombinant viruses. The measurement of virus titers was done by plaque assay[5]. Briefly, fresh 293A cells in 6-well plates were infected with different dilutions (ranging from $10^{-1}$ to $10^{-10}$) of the recombinant viral stock medium. After 6 h, the infected 293A cells were overlaid by sea plaque agarose and counted for the viral plaques after 15-day culture.

$5 \times 10^6$ of 293A-CR5-LacZ were plated in to each 100 mm dish, cultured overnight and infected with 100-200 p.f.u./dish. After 6 h infection, cells were washed and 10 ml/dish of fresh medium with sea plaque agarose (at 1% final concentration) were added in the presence or absence of 200 ug/ml of inducer cumate. Seven days later, additional 5 ml of the same conditional medium was overlaid on the dishes and culture was continued for another 7-10 days until the viral plaques formed. 3 ml of LacZ enzyme substrate (2% blue-Gal solution) mixed with fresh sea plaque agarose medium was overlaid on the surface of each dish and incubated overnight. Only the viruses from plaques that were blue under the induction of cumate were picked and were plaque purified three times for further analysis.

Example 4

Analysis and Characterization of Reverse Mutant of CymR

The reverse CymR mutant sequence was obtained by PCR amplification from the picked viruses mentioned above. Briefly, 293A cells were infected by the plaque purified viruses. Viruses were harvested in the culture medium and three cycles of freezing and thawing were used to release the amplified viruses. 1 ul of the supernatant was applied as a template for the 50-ul volume of PCR reaction with the same primers as mentioned before. The resulting PCR fragments were digested with BglII and NotI and ligated into the BglII-NotI restricted plasmid pAdCMV5cTA to replace the wild type CymR. Transformations were then performed using *E. coli* Dh 5α.

293A stable cells were generated using lentiviral vectors expressing CymR protein, (Lenti-CymR), reverse rcTA fusion protein (Lenti-rcTA), and reporter GFP protein (Lenti-CR5-GFP). Simply, 293A cells were infected with the mentioned lentiviruses. In order to optimize the efficacy of the transgene integrations to host cell chromosomes, the infection was carried out three times at 24 h intervals.

For generation of stable CHO cells, 10 ug of linearized plasmid pAdCMV5rcTA- and 10 ug of pPuro (Clontech, CA) for selection were co-transfected to $10 \times 10^6$ CHO cells using 40 ul of PEI in 100 mm dish. One day after the transfection, the cells were washed with PBS and resuspended in CD CHO culture medium and plated into 96-well plates with the ratio of 3000 cells per well under 6 ug/ml of puromycine selection. Three weeks later, the positive clone pools were verified by infection of adenoviral vector CR5-GFP in the presence or absence of inducer cumate. The verified positive pools were subcloned using limiting dilution of 1-1.5 cells/well in 96-well plates and verified again by infection with an adenovirus AdCR5-GFP using the same condition as described above.

Stable cells harbouring chromosomally integrated copies of the LacZ reporter construct pAdCR5-LacZ were transiently transfected with 400 ng of reverse mutant pAdCMV5rcTA plasmid DNA and 2 ug of carrier DNA mixed with 4.8 ul of PEI under the induction of 200 ug/ml of cumate. As a comparative control, the wild type of pAdCMV5cTA DNA was transiently transfected into the 293A stable cells with the same conditions as described here. Two days later, the transfected cells were subjected to β-galactosidase staining using the β-Galactosidase Reporter Gene Staining Kit (Sigma). Alternatively, the quantitative determination of β-galactosidase activity in the transfected cells was performed using β-Gal ELISA kit (Roche). Briefly, the transfected cells were washed with PBS, harvested by centrifugation and lysed by cell lysis reagent. 50 ul of cell extract and 100 ul of substrate reagent were mixed into a microtiter plate and incubated for 15 min at room temperature with gentle rocking. 50 ul of initiation reagent was added to each well and the measurement of the light reaction was performed. Seap activity was determined as follow. The enzymatic activity was measured at 37° C. using a microplate reader Spectro max 250 (Molecular Devices Corp, Sunnyvale, Calif.). Briefly, the samples were heated at 65° C. for 5 min to inactivate the endogenous Seap. Aliquots were diluted to a final volume of 50 μl of growth medium and transferred into 96-well plate.

50 µl of 2×SEAP buffer (1M diethanolamine pH 9.8, 2 mM $MgCl_2$, 10 mM 1-homoarginine and 20 mM p-nitrophenyl phosphate) was added and the increase of optical density at 420 nm ($OD_{420}$) was determined every min for up to 40 min. The variation of $OD_{420}$ as a function of the time corresponds to the SEAP activity (OD/min).

Stable CHO cells expressing rcTA transactivator were infected by AdVCR5-GFP at MOIs 100 and 500 in the present or absent cumate (30 ug/ml), and incubated at 30° C. or 37° C. respectively. After 48 h infection, all of the cells were harvested, fixed (0.2 ml paraformaldehyde/ml medium, and filtered for FACS analysis.

For lentiviral infection analysis, normal 293A cells were co-infected by lentiviruses CMV5-CuO-rcTA and CR5-GFP. 48 h later, all infected cells were subjected to FACS analysis following the same procedure as mentioned above.

Virus infected CHO or 293A cells were harvested with cultured medium and fixed for 1 h by adding 0.2 ml of 10% of methanol free formaldehyde, into 0.8 ml cell mixture. After filtration to remove cell clump, FACS was performed using FACScalibur from Becton Dickinson (San Jose, Calif.). Analysis was done on a total of 10,000 cells in each gated region using CellQuest software. The percentage of positive green cells were determined.

Example 5

Generation of an Efficient Stable 293A Cell Line for Screening and Analysis

Previous experiments had already shown that a stable cell line with optimized sensitivity for cumate induction is important for further library screening. The inventors made use of the 293A cells as the parent one and chose the plasmid pAdCR5-LacZ-neo constructed[19] with the strong promoter CR5 and the reporter LacZ gene. CR5 is a chimeric promoter[19] and it is recognized by the fusion transactivator cTA, CymR-VP16[19]. The binding of cTA to promoter CR5 is interfered by the inducer, a small non-toxic molecule cumate, which results in the silencing of the reporter gene. The inventors used neomycin G418 for the selection of positive cell clones and analyzed by transferring cTA-expressing plasmid into the cells.

In general, screening and analysis of mammalian positive cell clones in such large numbers by transient transfection can be inefficient, may have low sensitivity and be time consuming. The inventors have previously developed an efficient system for this analysis, the adenovirus vector expressing cTA fusion protein. More than 100 positive clones were screened by adenovirus infection and analyzed under the induction of cumate with the concentration of 200 ug/ml. Amongst them, one clone displayed the strong expression of reporter LacZ gene with significant 40-fold induction ratio (FIG. 1).

Example 6

Establishment of Adenoviral Libraries with CymR Random Mutants Using the Positive Select System Random mutagenesis is a powerful tool to modify proteins for desired purposes[6]. Amongst the different techniques, error prone PCR is the one for generating amino acid substitution in proteins by introducing mutations into a gene during PCR. This technique allows us to generate large sized libraries. However, efficient screening of the library in mammalian cells was a potential bottleneck for the application of this technique. The inventors have previously developed a very useful system, adenovirus positive select system[4], highly suitable for searching for CymR protein reverse mutants.

In order to optimize the binding efficacy of fusion transactivator cTA, before doing PCR random mutagenesis of CymR protein, the inventors designed a five-Glycine small peptide as a hinge linking to the two proteins, CymR and VP16. This is based on the theory that a linker between two domains of a protein may be necessary for protein flexibility and therefore for activity. The result showed that the activity of the modified transactivator cTA-linker is similar to the original one. However, the new version with the linker was used as the base for the generation of the mutants since it was anticipated that the presence of the linker could have a beneficial influence on the binding activity of the mutated cTA.

In the next step, the CymR gene was amplified by PCR under mutagenic conditions as described by the manufactures instruction. Three PCR products with different mutation frequencies ranging from 0-3 to 7-16 mutations/kb were obtained and subcloned into plasmid pAdCMV5cTA to replace the wild-type CymR. Three different frequency libraries with approximately $2.5 \times 10^5$ recombinant *E. coli* clones were established. The plasmid pools were amplified and purified as described previously to generate adenoviral libraries by using the positive selection system. Since the size of recombinant *E. coli* libraries were over the capacity of adenoviral positive selection system, the inventors conducted infection/transfection three times in different dishes to maximise the diversity of the recombinant adenoviral libraries.

Example 7

Screening for Novel rcTA Alleles in Recombinant Adenoviral Libraries

Figure 2A:
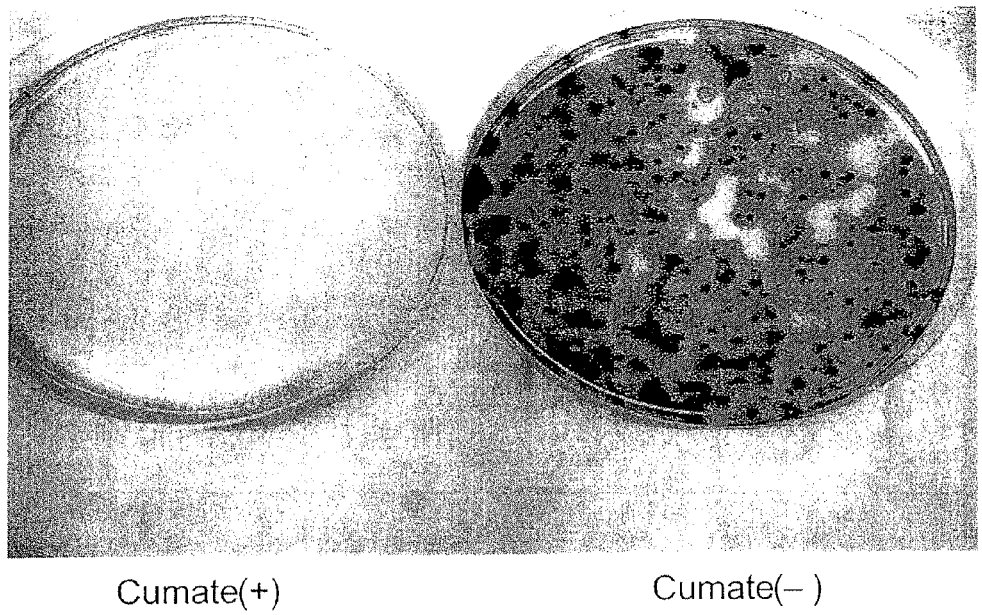
FIG. 2: Adenoviral plaque comparisons from wild type cTA and recombinant mutated cTA libraries. Stable 293A-CR5-LacZ cells were infected by AdVCMVcTA or recombinant AdVCMV-mut-cTA in 100 mm plates respectively with 200 p.f.u. under the conditions of absence or presence 200 ug/ml cumate. (A) Recombinant virus AdVCMVcTA, with cumate inhibition, no blue viral plaques appear in the plate compared with the one in the absence of cumate, which displays many blue viral plaques. (B) Screening of Library No. 3: CymR mutants changed the features of cTA such that with cumate, a few blue plaques are visible in the plate. In contrast, several blue plaques are visible in the plate without cumate addition.
Figure 2B:
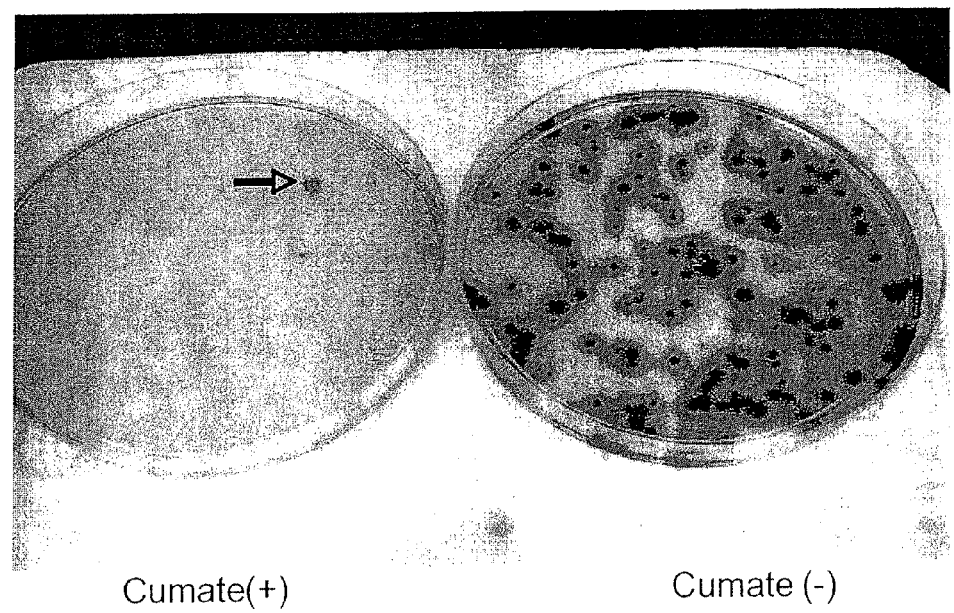
Figure 3A:
FIG. 3: Induction characteristics of various cTA mutants. Stable 293A-CR5-LacZ cells were transiently transfected with plasmids pAdCMV5-1-1BcTA, pAdCMV5-3-1BcTA and pAdCMV5rcTA respectively. Each transfection carried out with 2 ug of carrier DNA and 400 ng of plasmid DNA. As a positive control, the transfection of wild type pAdCMV5cTA was performed under similar conditions. Two days later, the transfected cells were subjected to β-galactosidase staining using the β-Galactosidase Reporter Gene Staining Kit. (A) Mutant 1-1B almost diminished the transactivator activity with the phenotype of no expression of β-galactosidase activity with or without cumate induction. Mutant 3-1B displayed a completely reversed phenotype of 1-1B mutant. Regardless of the presence or absence of cumate this mutated transactivator always initiated the reporter LacZ gene expression. (B) Mutant 3-4C revealed the reverse function compared with the wild type transactivator cTA. Under the induction of cumate, mutant 3-4C turned the reporter LacZ gene on, vice verse.
Figure 3A:
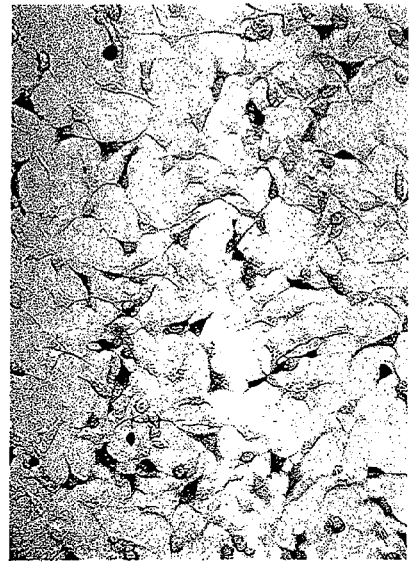
Figure 3A:
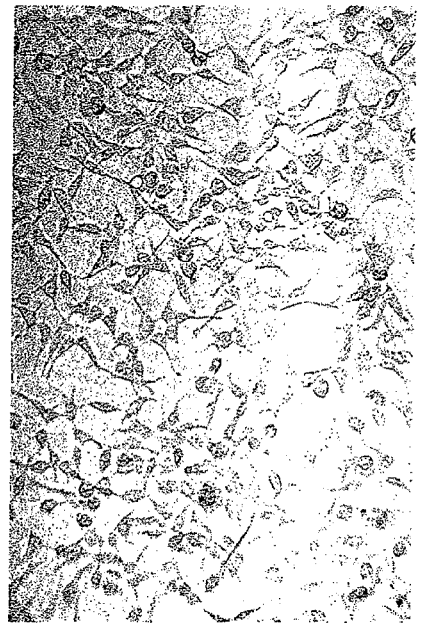
Figure 3A:
Figure 3B:
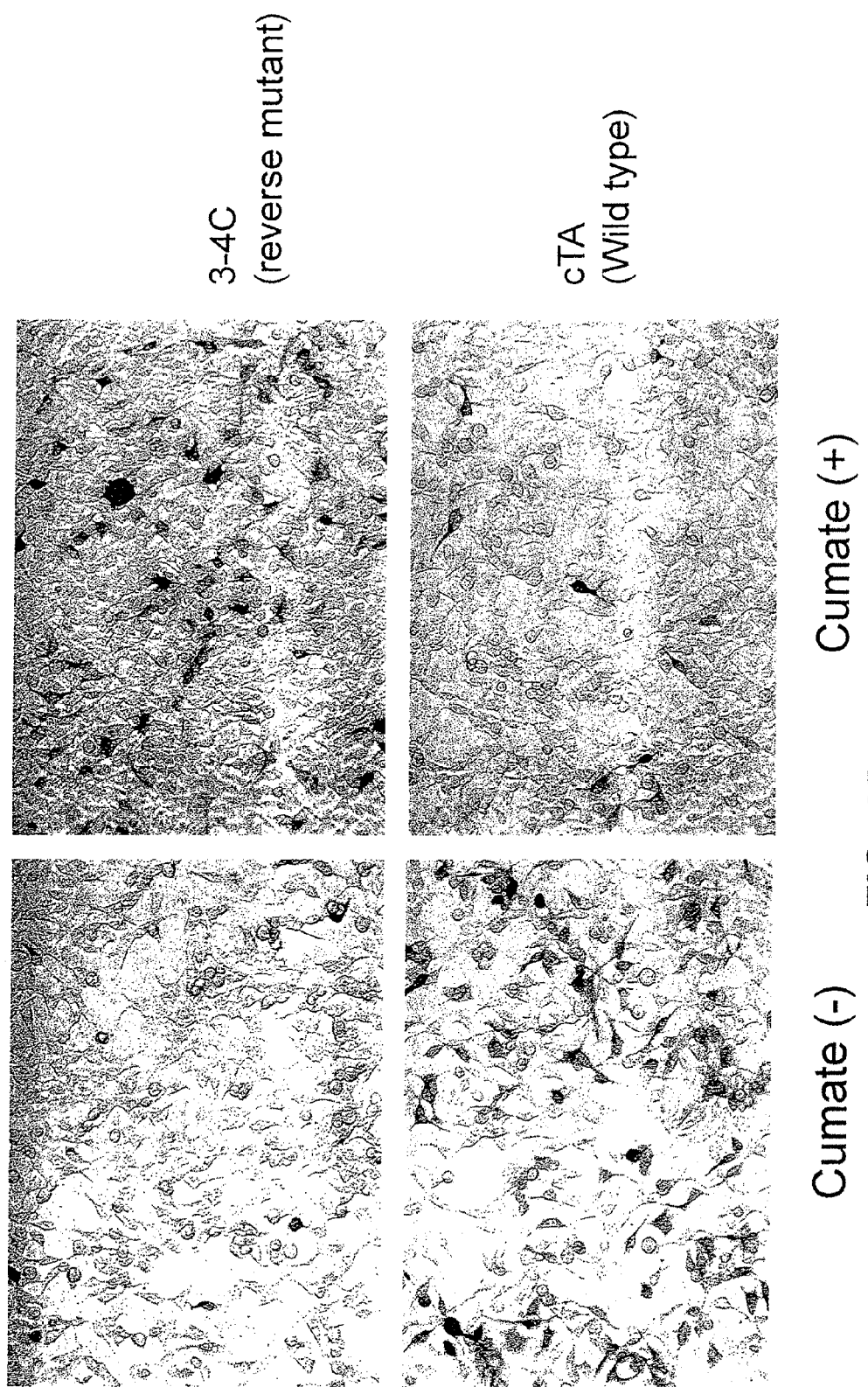

The inventors developed an efficient screening procedure found to be suitable for the identification of cTA/rcTA variants with adenovirus in 293A cells[7]. This is based on the concepts that adenovirus replication and amplification in mammalian cells needs two important genes, E1 and PS. The inventor's recombinant adenovirus libraries lack the E1 gene since it is replaced by the transgenes and PS gene. However, 293A cells contain the trans E1[7], which confers 293A cell to be an ideal candidate for screening the recombinant adenoviral libraries. In addition, since the stable 293A cell genome harbors reporter LacZ gene regulated under CR5 promoter, it is therefore highly suitable for isolating the target recombinant adenoviral plaques, amplify and purify them. FIG. 2 shows the results. Compared with the plate containing the blue wild type of cTA viral plaques under the condition of absence of cumate, the plate of recombinant viral libraries, with the same condition as the wild type one, displayed much less blue plaques due to the mutagenic CymR protein.

The inventors searched for reverse CymR mutants, which meant that the phenotype of viral plaques should also be reversed: i.e. the appearance of the blue plaques under the induction of cumate. Approximately 60,000 plaques were screened and ten reverse phenotypes of blue plaques were obtained, amplified and purified. Moreover, the ten plaques of viruses were subjected to PCR reaction for amplifying the mutated CymR coding sequences that were subsequently re-inserted into plasmid pAdCMV5cTA to substitute the wild type CymR. Further transient transfections were performed to verify the genotype mutation of CymR protein and confirm the mutations by sequence analysis. Finally, three mutated CymR with three different properties were obtained. As shown in FIG. 3, the mutant named 1-1B exhibited little transactivator function since CymR protein no longer bound to its corresponding DNA-binding element of CR5 promoter. Therefore, no blue 293A cells were apparent. Interestingly, the second mutant 3-1B displayed the complete reverse phenotype. Regardless of the presence or absence of inducer cumate, the cTA transactivator always kept high activity to initiate reporter LacZ gene expression. Comparison with the wild type cTA shown the blue cells in the absence of cumate, the third mutant, named 3-4C, revealed that it possessed the property of reverse cTA, in that, under the induction of cumate, the transactivator rcTA binds to CR5 promoter and initiated LacZ gene expression, vice verse. All of the mutations contributing to the three phenotypes of mutated CymR proteins are listed in Table 1.

TABLE 1

Mutations contributing to the different phenotypes of CymR-Vp16

| Transactivator | Amino acid exchanges |
| --- | --- |
| 1-1B null mutant | $Thr^{53}$ $Arg^{113}$ $Val^{142}$ $Gly^{144}$ $Ile^{175}$ $Cys^{176}$ |
| 3-1B constitutive on mutant | $Arg^{80}$ $Cys^{139}$ |
| 3-4C reverse mutant | $Val^{125}$ $Gly^{142}$ $Ile^{144}$ |

Example 8

Characterization of the Reverse Transactivator with Different Methodologies

Figure 4A:
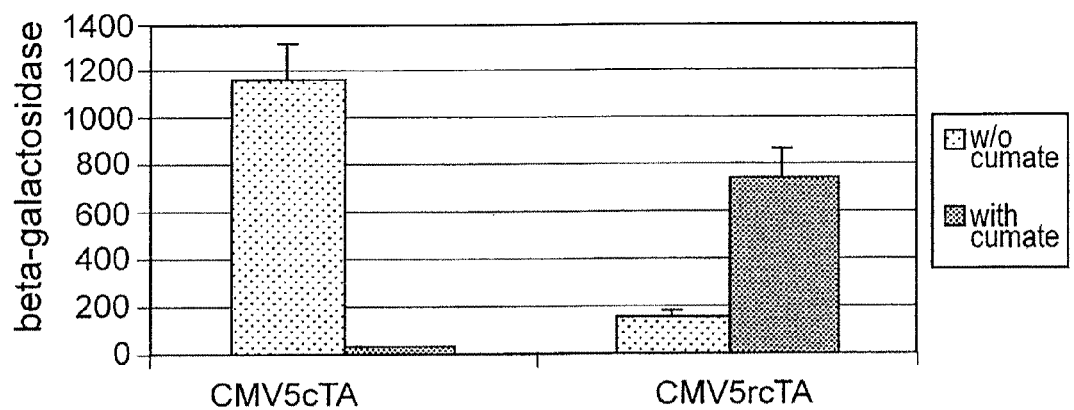
FIG. 4: Comparison of cumate induction efficiency between transactivators cTA and rcTA. (A) transient transfection: Stable 293A-CR5-LacZ cells were transiently transfected with plasmids pAdCMV5cTA and pAdCMV5rcTA with 1 ug of a plasmid coding for the cTA or the rcTA and 2 ug of the pAdCMV5SeapDCGFP. Transfections were done in triplicate, in the presence or absence of 200 ug/mL of cumate. After 48 h cultivation, the cells were harvested and β-galactosidase activity was analyzed from the cell extracts using β-Gal ELISA Kit and seap was measured. Seap levels were used as control to normalize the transfection efficiency. The figure shows the response to cumate induction of cTA-linker and rcTA-linker. The errors bars are standard deviation. (B) Activity of rcTA in a stable pool generated by Lentivirus infection: Normal 293A cells were co-infected by lentiviral vectors encoding CMV5-CuO-rcTA and CR5-GFP respectively. Two days later, the cells were harvested and fixed by using final concentration of 2% methanol free paraformaldehyde. Before FACS analysis, the fixed cells were filtered to remove the cell clumps. The result shows an average induction factor of almost 20-fold in a population of stable clones.
Figure 4B:
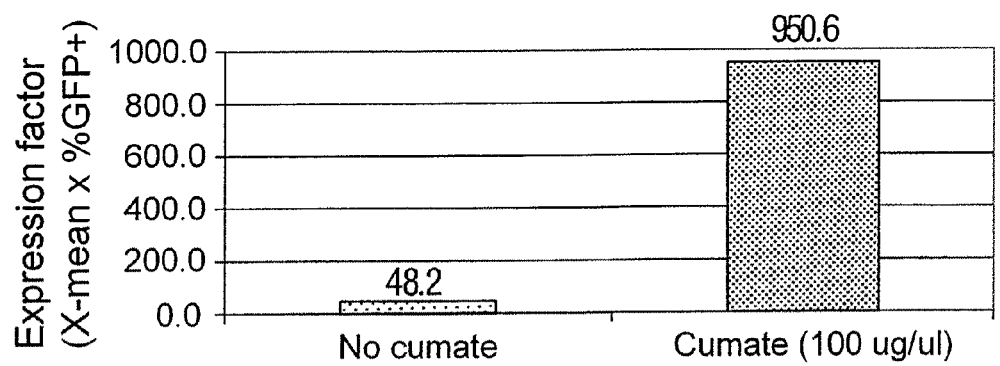
Figure 5:
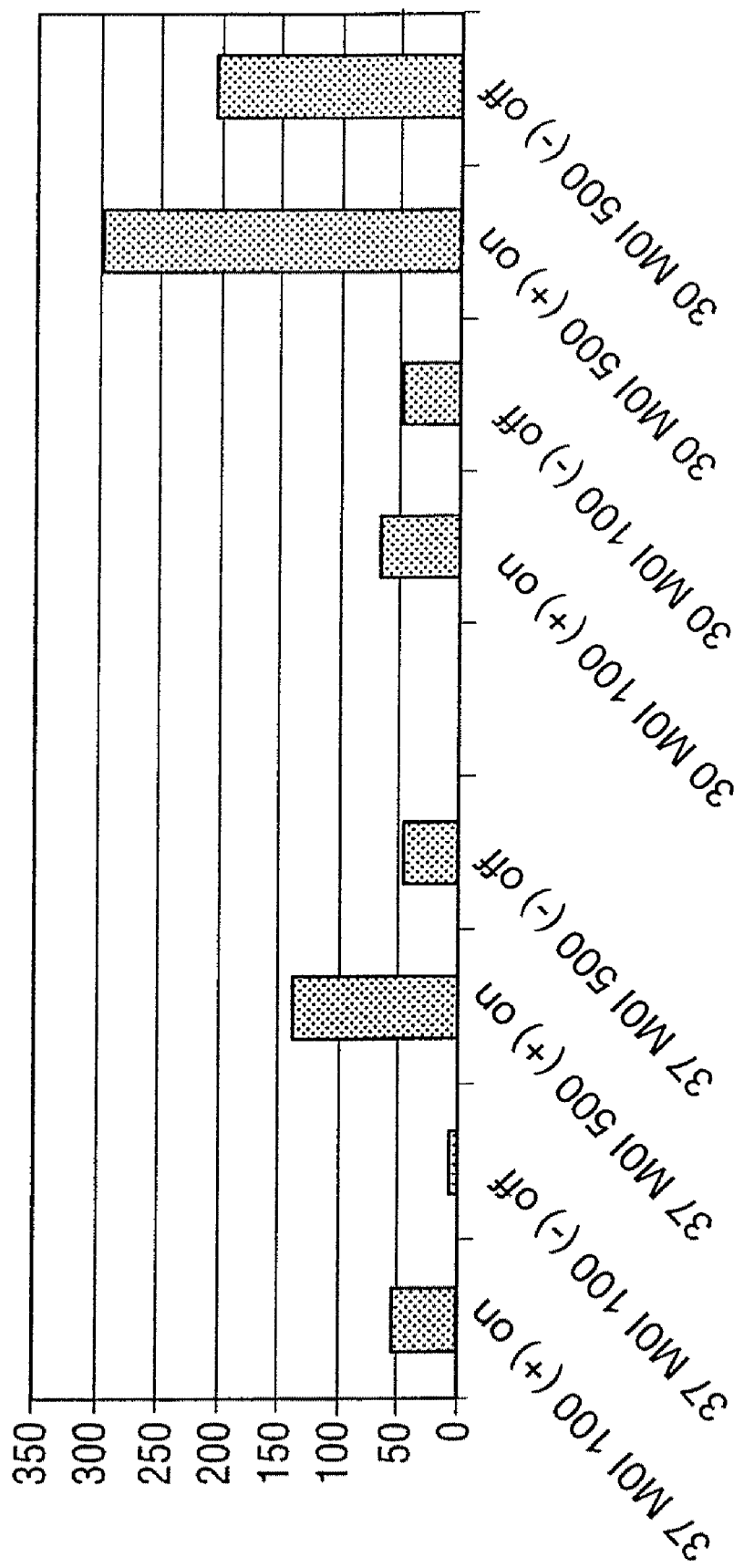
FIG. 5: Effect of temperature on rcTA activities in the stable rcTA CHO cells. Stable CHO-CMV5rcTA cells were infected with adenoviral vector AdVCR5-GFP at the MOIs 100 or 500 respectively, and were grown in CD CHO medium with or without cumate at the concentration of 30 ug/ml, and in the temperature of 30° C. or 37° C. respectively. After 48 h incubation, the cells were harvested, fixed and filtered, the same procedure as described as in FIG. 4B, and subjected to FACS analysis for reporter gene GFP expression initiated by rcTA transactivator. The result shows an induction factor of 1.5 to 2 fold at 37° C., much lower than in stable 293 cells (FIG. 4B). However, the induction of expression by cumate is no longer apparent at 30° C. while the overall expression is significantly increased.
Figure 6:
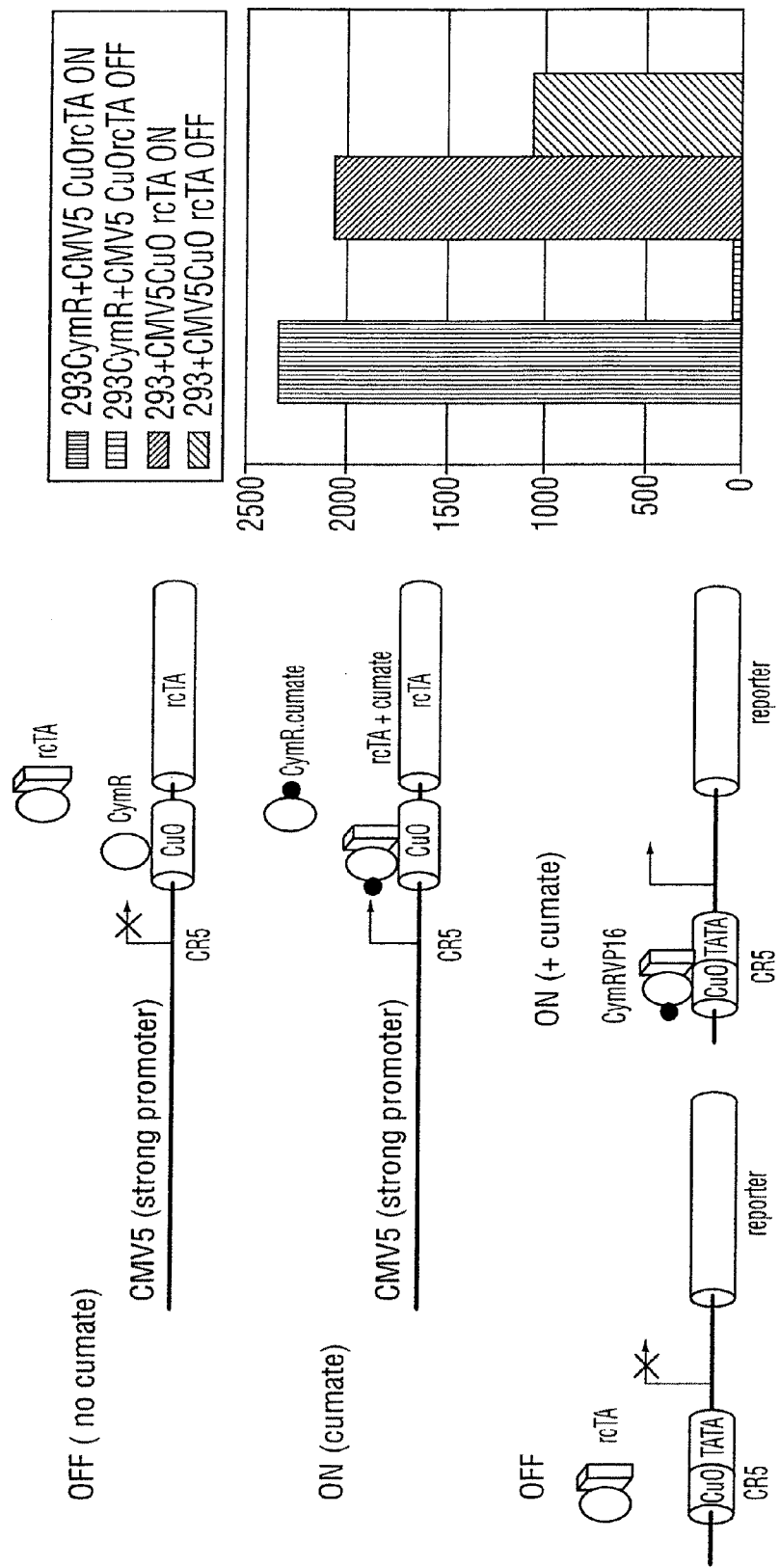
FIG. 6: Double regulation of rcTA-switch system. Left panel represents the configuration in the double regulation in which rcTA expression is controlled by CymR binding to the CuO operator downstream of the CMV5 promoter as the first level of regulation. Upon addition of cumate, rcTA is produced and binding of cumate to rcTA activates the induction of the CR5 promoter that then expresses the reporter gene. This constitutes the second level of regulation. In the right panel 293A-CymR cells or normal 293A cells were transiently transfected with 500 ng of plasmid pAdCMV5CuO-rcTA, 500 ng of plasmid pAdCR5-LacZ and 2 μg of seap plasmid as internal control respectively. Then, cells were cultivated in DMEM medium containing 200 ug/ml of cumate for 48 h. After harvesting the cells, β-galactosidase and seap activities were measured.

To further examine the transcriptional activity of the reverse cTA, two different levels of experiments were carried out. First, a β-Gal reporter gene assay (chemiluminescent) was conducted by transient transfection of rcTA or cTA plasmids, pAdCMV5cTA-linker or pAdCMV5rcTA-linker, into the stable 293A-CR5-LacZ cells respectively, name of stable cell line and cultivation in the presence or absence of cumate for 48 h. As shown in FIG. 4, a 10-fold increase in activation of rcTA was observed with the induction of cumate, compared with non-induction rcTA. The reverse transactivator rcTA displayed almost the same level of activity as the wild type cTA. The second experiment for estimating the rcTA activity was performed by using lentiviral vectors AdCMV5-CuO-rcTA and AdCR5-GFP. Normal 293A cells were infected with MOIs 50 or 20 respectively, and cultivated at 37° C., 5% $CO_2$ for 48 h. Since in this experiment, the reporter gene was GFP, all of the infected 293A cells were analyzed by FACS for verifying the activity of the transactivator rcTA. As expected, the results showed that under the induction of cumate, the transcriptional activity of rcTA was about 19-fold higher than that of non-induction rcTA (FIG. 6).

Example 9

Regulation of the Transgene Expressions by rcTA in Stable CHO Cells

Chinese hamster ovary (CHO) cells have been widely used for the production of therapeutic proteins[8,9]. The application of using inducible gene switch system for stably expressing desired genes have been reported. The inventors have previously generated stable CHO cell lines expressing the therapeutic proteins under the regulation of cTA gene switch system. Compared with Tet-switch in which the large amounts of activator were required to achieve the required protein expression level, cTA-switch is a more efficient system for high level protein expression in all tested cells including CHO (data not published). However, removal of the inducer cumate for the induction of protein expression in cTA-switch system is a cumbersome process for large-scale production.

In order to extensively exploit the application of cTA gene-switch system, attempts of establishment of stable CHO cells constitutively expressing reverse transactivator rcTA were made by co-transfecting plasmids pAdCMV5rcTA and pPuro into CHO cells. After a three-week selection with puromycin, the stable CHO cell pools were subjected to subcloning for obtaining the stable CHO-rcTA cell line, and analyses for the transcriptional activity by infection of adenovirus bearing reporter expression cassette, AdVCR5-GFP. Surprisingly, the results showed that the activity of transactivator rcTA in CHO cells was different from 293A cells and the cultivated temperature is another factor to impact rcTA activity (FIG. 6). With FACS analysis of reporter GFP gene expression, the results indicated that the ratio of induction by cumate in stable CHO cells was lower compared with the induction in the stable 293A cells, only reaching 2-3 times of induction. Moreover, at 30° C. the average expression level of GFP protein in the stable CHO cells was higher than the expression level of GFP at 37° C., but the induction ratio was less significant (almost no induction). This might be due to two possibilities. First, the reverse transactivator rcTA is controlled by enhanced promoter CMV5[10] that possesses the characteristic that its activity is higher at 30° C. than at 37° C. in CHO cells. The more transactivator rcTA expression, the more reporter GFP gene initiated, and the less induction ratio obtained because of the high concentrate rcTA protein as mentioned before. Second, the screening of adenoviral libraries for reverse CymR protein was performed at 37° C., and the impact of changing temperature might contribute to the change of the mutated CymR configuration, and therefore, resulted in reducing the affinity of reverse CymR binding to its DNA binding element in CR5 promoter.

Example 10

Double Regulation of rcTA Gene Switch in Large-Scale Protein Production

Given the fact that single regulation of reverse cTA to gene expression might be not sufficient for high level, large-scale production of therapeutic proteins, the inventors considered that double regulation of rcTA gene switch might be a suitable tool for complementing this system. To do so, the inventors constructed a plasmid with CymR protein-binding element named CuO down streamed to CR5 promoter. The idea is that regulating the expression of rcTA using the CymR protein would reduce the expression of rcTA in absence of cumate thereby reducing the expression of the gene of interest controlled by the CR5 promoter. Since both CymR and rcTA proteins are activated by cumate, upon addition of cumate, rcTA would be expressed from the CMV5CuO promoter and in turn activate the expression of the gene of interest controlled by the CR5 promoter. This strategy can work only because the CymR and rcTA proteins display an opposite response to cumate induction (FIG. 6). As expected, the double regulation of rcTA-switch resulted in dramatically increasing the induction ratio in stable 293A-CymR cells compared with the single regulation one in normal 293A cells (FIG. 6). Taken together, it is important and possible to generate stable cell lines integrated with double regulated rcTA-switch system for regulation of large-scale expression of therapeutic proteins. In addition, under the regulation of the rcTA-switch system, the desired gene expression could reach much higher levels at 30° C., in which the induction of cumate was diminished, while the induction ratio at 37° C. appeared high but the protein expression level was lower. This discovery offers another opportunity for tightly controlling the protein expression in large-scale mammalian cell culture, such as CHO cells. Simply, stable CHO-CymR cells with double regulated rcTA-switch would be induced at 37° C. to reach the desired induction level, and then the temperature could be turned down to 30° C. for high protein expression. Since the release of CymR by cumate will not be diminished at 30° C. (data not shown), the protein expression may continue until the ideal level is achieved.

The inventors have observed that, at least in selected embodiments, rcTA can activate the CR5 promoter to levels similar to what is obtained with cTA. However, for comparable induced levels, the induction factor observed for the reverse system is not as high as that obtained with the cTA system. In an attempt to further improve the reverse cumate gene switch system, the inventors have developed further preferred embodiments of the invention involving a double regulatable system and applied it generate stable cell lines (e.g. 293 and CHO cell lines) tightly controlling and yet highly expressing reporter genes such as GFP and Seap. Such experimental results are presented in subsequent examples.

Example 11

Generation of 293rcTA/CR5-SEAP-IRES-GFP and 293-CymR-rcTA/CR5—SEAP-IRES-GFP Stable Pools 293 or 293-CymR stable cells were transduced with reverse rcTA fusion protein lentiviral vector pRRL. cppt.CMV5-rcTA.WPRE and lentiviral vector pRRL. cppt.CMV5-CuO-rcTA.WPRE respectively to generate 293rcTA and 293-CymR-rcTA. These pools were then transduced with (Lenti-CR5-SEAP-IRES-GFP) to generate 293rcTA/CR5-SEAP-IRES-GFP and 293-CymR-rcTA/CR5-SEAP-IRES-GFP stable pools. In order to optimize the efficacy of the transgene integrations to host cell chromosomes, the infections were carried out three times at 24 h intervals.

Example 12

Generation of 293SF-CymR-rcTA $9 \times 10^4$ 293SF-CymR cells were plated in a 24 well plate. They were transduced with 500 µl of pRRL.cppt.CMV5-CuO-rcTA.WPRE lentiviral vector supernatant. The pool of cells was sub-cloned by limiting dilution in 96-well plates (HSFM 2% FBS). The clones were screened by measuring reporter gene expression (GFP) from an adenoviral reporter, AdCR5-GFP in the presence and absence of cumate (50 µg/ml).

Example 13

Generation of CHO-CymR/rcTA

To generate double regulated stable CHO cells, a triple co-transfection in which 10 µg of linearized plasmid pAdCMV5CuO-rCTA, 10 µg of linearized plasmid pAd-CMV5-CymR and 10 µg of pPuro (Clontech, CA) were applied. After the transfection the cells were plated in 96-well plates and puromycin was added at 6 µg/mL. More than 300 clones were picked and analyzed for expression of rcTA by infection with an adenovirus encoding GFP under the control of the CR5 promoter (AdV-CR5-GFP) at a MOI of 100. The 2 best clones (10 and 300) were further subcloned by limiting dilution and the screen for rcTA expression as described above. The best clone (CHO-10#35) was selected for further analysis. To stably integrate GFP and SEAP reporter genes in CHO-10#35, these cells were transduced with a lentiviral vector carrying the SEAP and GFP reporter genes co-expressed from an IRES under the control of the CR5 promoter. Briefly, $1 \times 10^4$ stable CHO-10#35 cells were plated into a 96-well plate one day before being transduced with the Lenti-CR5-SEAP-IRES-GFP at an MOI of 1.3. The transduction was repeated twice to increase the proportion of transduced cells in the population. To further enrich for transduced cells, cumate was added and GFP+ cells were sorted by FACS.

Example 14

Production of Lentiviral Vectors

Ten million cells were plated in a 150 mm dish, the day before being transfected. The media of these cells was changed 2 h before the transfection (16 ml HSFM with 1% FBS). 80 µg of PEI was mixed with 40 µg DNA in 1.5 ml HSFM and incubated for 15 minutes at R.T. before being added to the cells. The cell culture medium was changed 4 h after the transfection (18 ml HSFM 1% FBS+1 µg/ml doxycycline and 50 µg/µl cumate). Cell culture supernatants were harvested 48 h later and fresh growth medium was added to the cells to continue lentiviral vector production. The two supernatants (48 h and 72 h) were centrifuged at low speed to remove the cells and filtered with a 0.45 micron filter. The resulting supernatant was centrifuged at 25 000 rpm for 2 h at 4° C. The viral pellets, resuspended in growth medium (DMEM or HSFM) were stored at −80°

Example 15

Figure 7:
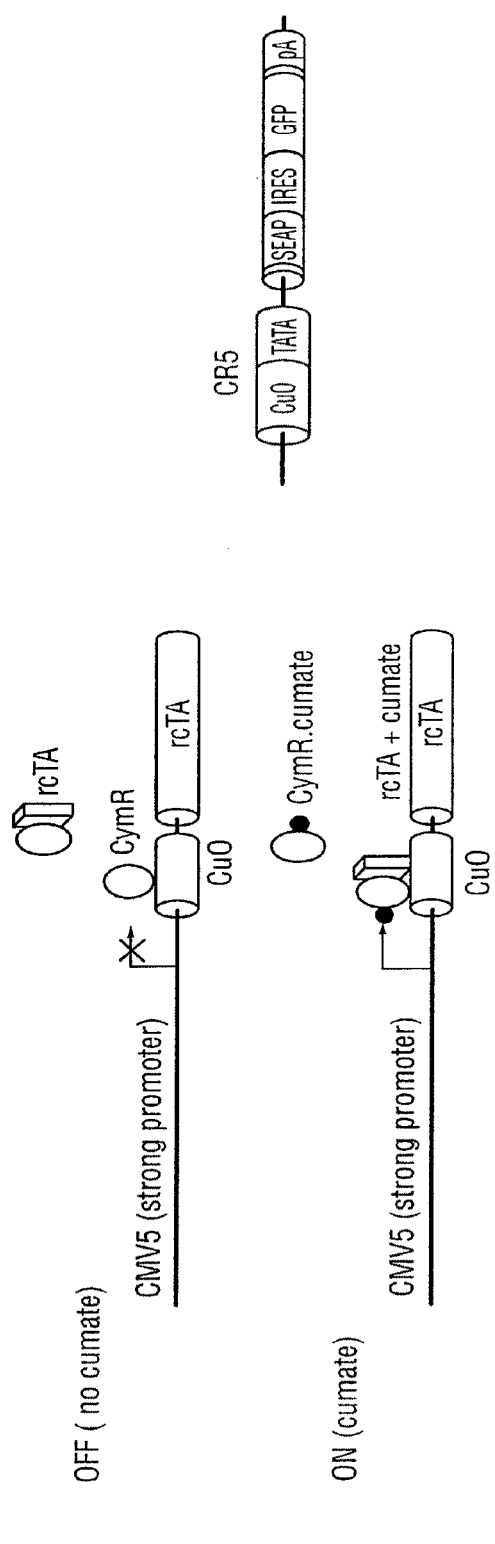
FIG. 7: Double regulation of rcTA-switch system in stable 293 pool cells generated by lentiviral vector transduction. Left panel represents the configuration of the double regulation in which rcTA expression is controlled by CymR binding to the CuO operator downstream of the CMV5 promoter as the first level of regulation. Upon addition of cumate, rcTA is produced and binding of cumate to rcTA activates the induction of the CR5 promoter that then expresses the reporter gene. This constitutes the second level of regulation. In the right panel, $5 \times 10^5$ stable pools of 293-CymR-rcTA/CR5-SEAP-GFP or 293-rcTA/CR5-SEAP-GFP cells were cultured for 48 h in the presence and absence of 25 ug/ml of cumate for 48 h and SEAP levels measured in the culture supernatants at the end of the incubation period. In 293-CymR cells, regulating the expression of the rcTA with the CMV5-CuO promoter allows the induction factor to be significantly increased while maintaining the same level of expression of the reporter gene.
Figure 7:
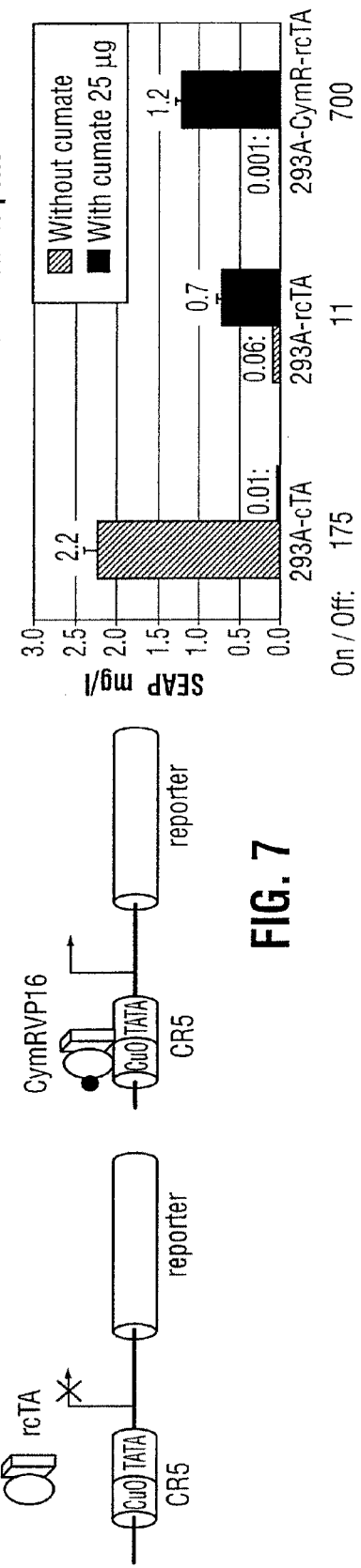

In 293-CymR Cells, Regulating the Expression of the rcTA with the CMV5-CuO Promoter Allows a Significant Increase in the Induction Factor while Maintaining the Same Level of Expression of the Reporter Gene Given the fact that in the absence of cumate, leaky gene expression was observed, the inventors regulated the expression of rcTA such that it would be lower in the OFF state than in the ON state. Thus rcTA expression was driven by the CMV5-CuO promoter, wherein expression from the CMV5 promoter can be inhibited by CymR binding to the CuO element. As expected, the double regulation of reporter gene expression resulted in dramatically increasing the induction ratio in both transient (FIG. 6) and stable 293A-CymR cells (FIG. 7) compared with the single regulation in normal 293A cells. It is noteworthy that in stable pools, the induction factor in the doubly regulated configuration is 4-fold better than in 293-cTA (700 vs 175 on/off factor).

Example 16

Selection of 293-SF-CymR/rcTA Clones

Figure 8:
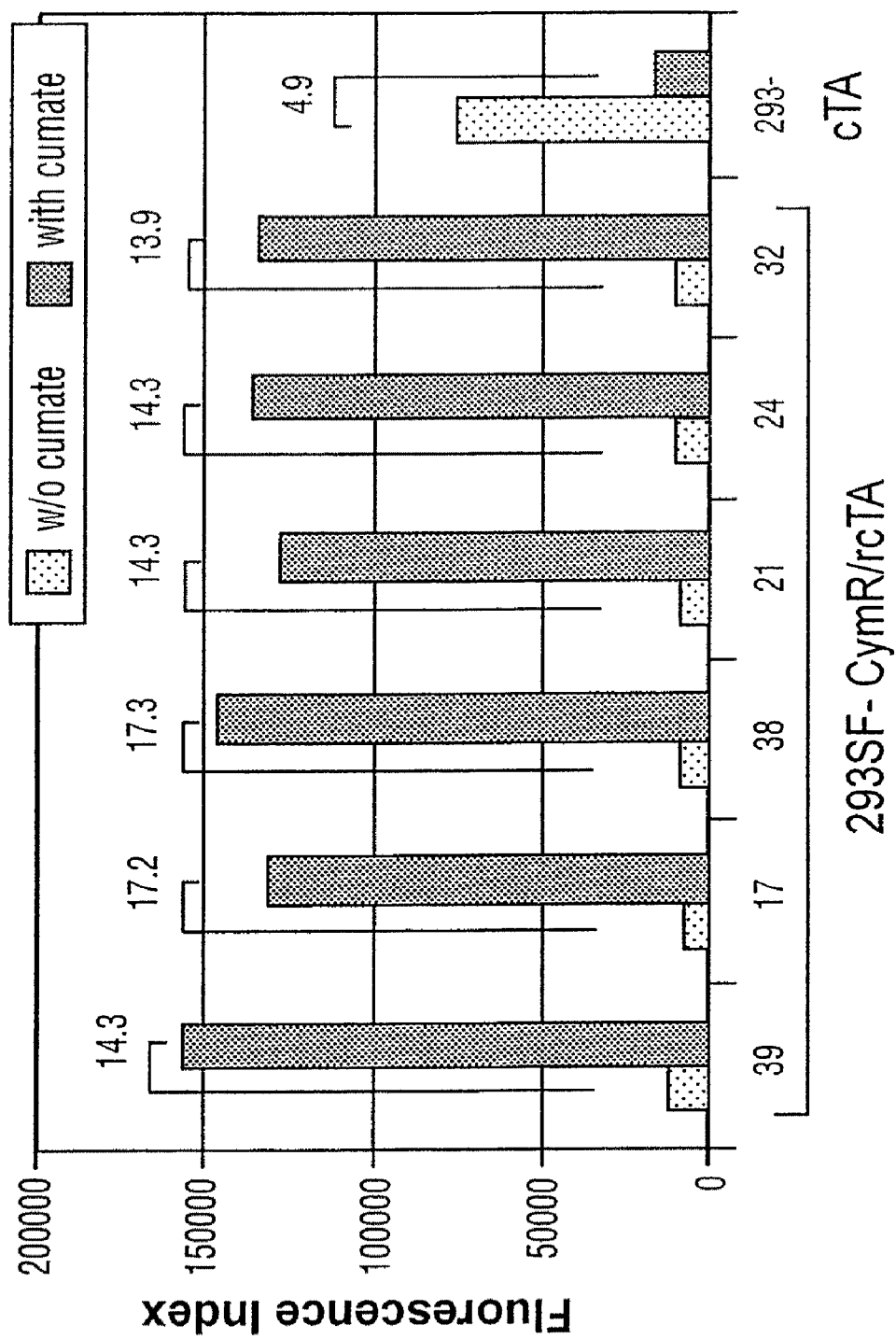
FIG. 8: Selection of 293SF-CymR/rcTA clones. 293-cTA and selected 293SF-CymR/rcTA clones were infected with AdCR5-GFP at a MOI of 10 and analyzed 48 h post-infection for GFP expression with or without 25 ug/mL of cumate. Numbers on bars indicate the ON/OFF ratio.

Since 293 cells adapted to grow in serum-free conditions (293-SF) (11), are advantageous for applications such as large-scale protein production, the inventors wanted to identify a clone exhibiting high-level expression and high ON/OFF ratios in this cell line. 293 SF-CymR/rcTA clones were infected with AdCR5-GFP at an MOI of 10 and analyzed for GFP expression 48 h post-infection, with or without the addition of 25 μg/ml of cumate. FIG. 8 shows the fluorescence index for 6 of the best clones and that for 293-cTA as a reference. Clone #38 was chosen for further studies because the level of activation was one of the highest and the ON/OFF ratio of 17.3 is the highest. Again using transient expression with adenoviral vector (AdV-CR5-GFP), the induction factor in the doubly regulated configuration is 3.5-fold better than in 293-cTA.

Example 17

Selection of CHO-CymR/rcTA Clones

Figure 9A:
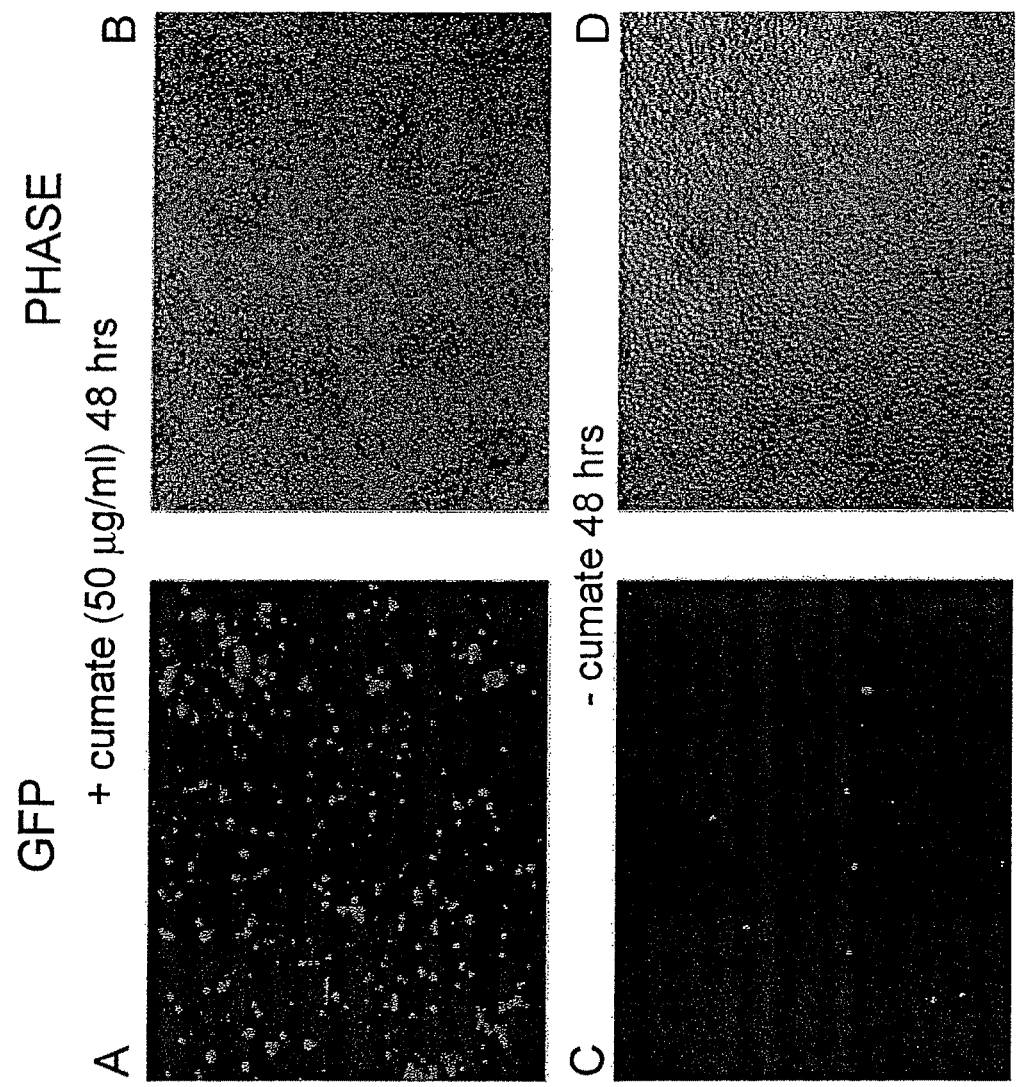
FIG. 9: High expression and tight regulation of GFP in CHO-CymR/rcTA clones A. CHO-CymR/rcTA clone #10 cells were infected with AdCR5-GFP and cultured in the presence and absence of 50 μg/ml cumate for 48 h. Fluorescence (GFP) or phase contrast micrographs of the cells under induced (+cumate) and un-induced conditions are shown. B. Selection of sub-clones of CHO-CymR/rcTA clone #10 and #300: CHO-CymR/rcTA clone 10 and clone 300 were subcloned by limiting dilution. The clones were infected with AdCR5-GFP in the presence and absence of cumate as described above. CHO-cTA clone 5F1 was used as a reference for induction level.
Figure 9B:
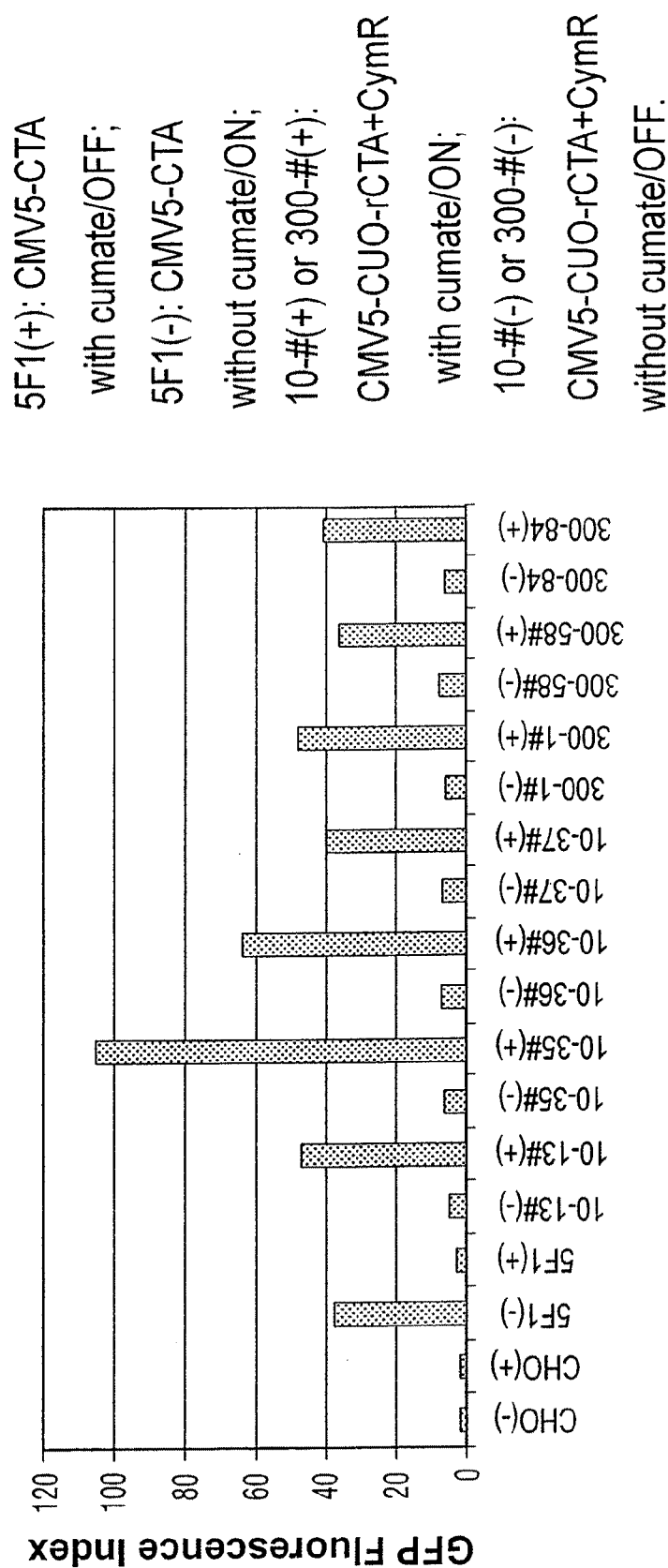

More than 300 CHO-CymR/rcTA clones were tested for high expression and tight regulation of GFP by adenoviral infection (AdVCR5-GFP). FIG. 9A shows the phase contrast and GFP fluorescence when one of the best clone (#10) was cultured in the presence and absence of cumate. In the presence of cumate, the rcTA activates high-level GFP expression. The two best clones, CHO-CymR/rcTA#300 and CHO-CymR/rcTA#10 were sub-cloned by limiting dilution. To identify a clone exhibiting high-level expression and high ON/OFF ratios CHO-CymR/rcTA#10 and 300 subclones were infected with AdCR5-GFP at an MOI of 10 and analyzed for GFP expression 48 h post-infection, with or without the addition of 25 ug/ml of cumate. FIG. 9B shows the fluorescence index for the best clones and that for CHO-cTA (5F1) as a reference. Clone 10-35 has been chosen for further studies because of the high level of activation and tight regulation of GFP expression.

Example 18

Figure 10:
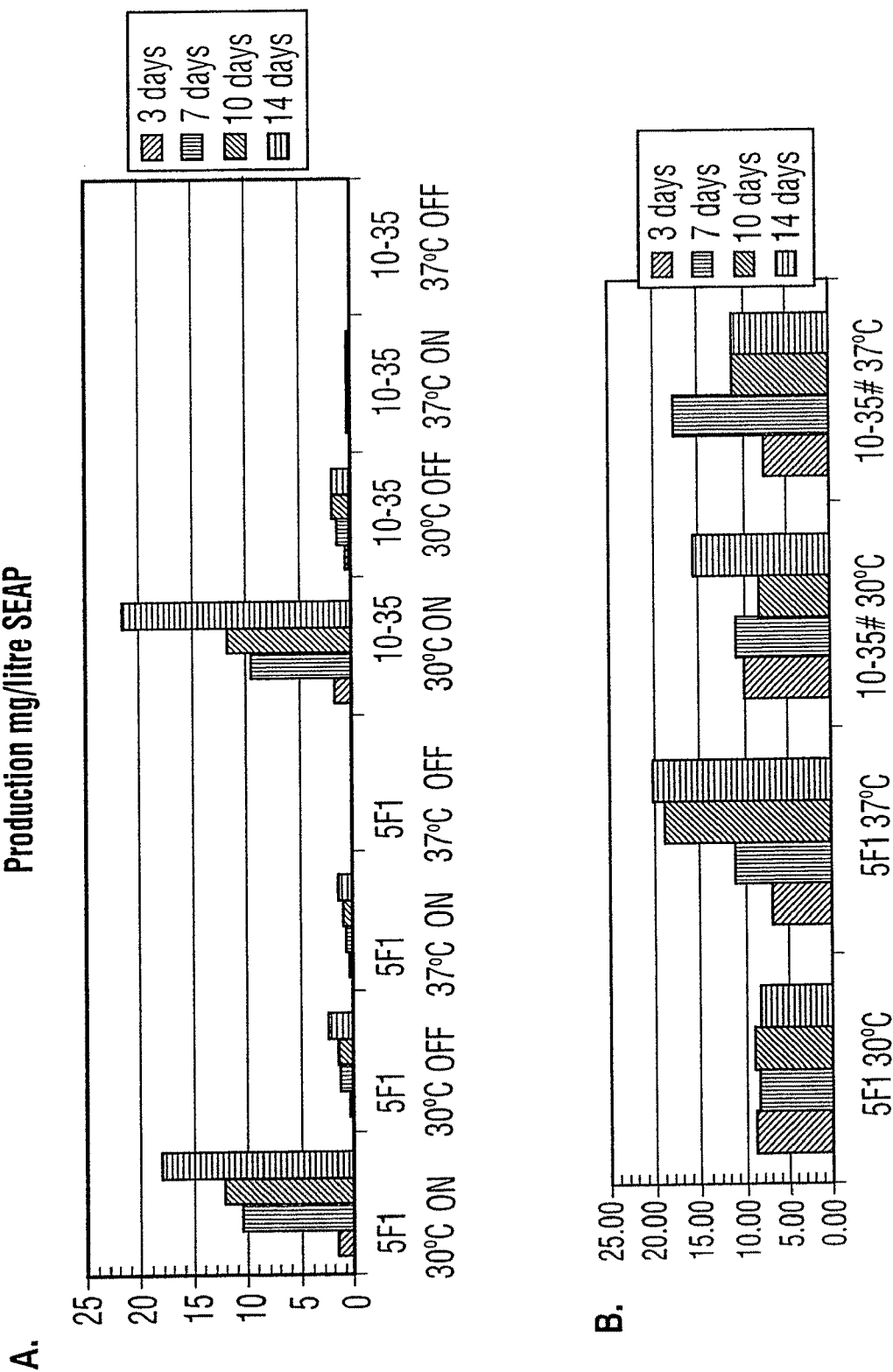
FIG. 10: Effect of temperature on the expression of the inducible genes in the stable CHO cells. Stable CHO pools CHO-CymR/rcTA/10#-35/CR5-SEAP-GFP and CHO-cTA/5F1/CR5-SEAP-GFP, were grown in CD CHO medium with or without cumate at the concentration of 50 μg/ml, and at the temperature of 30° C. or 37° C. respectively. After 3, 7, 10 and 14 day incubation, SEAP expression was measured in the cell culture medium. Panel A shows the levels of SEAP production in stable CHO-cTA/5F1/CR5-SEAP-GFP and CHO-CymR/rcTA/10#-35/CR5-SEAP-GFP cells at 30° C. and 37° C., and panel B shows the induction ratios.

Effect of Temperature on the Activity of the Doubly Regulated rcTA Gene Switch System in Stable a Pool We have previously described that in CHO-cTA cells the expression level of the CR5 promoter was increased by 5-10 fold when the cells were shifted at 30° C. (19). This represents a significant asset for large-scale protein production in CHO cells. We therefore examined whether the selected CHO-CymR/rcTA clone (CHO#10-35) exhibited the same property. Stable pools of CHO-cTA (5F1) and CHO-CymR/rcTA (10-35) expressing the reporter SEAP and GFP genes from the CR5 promoter were established using lentiviral vector transduction as described above. Both pools were enriched by FACS to similar levels of GFP positive cells (about 80%). FIG. 10A shows the results of SEAP gene expression at days 3, 7, 10 and 14 post-induction of the stable pools. FIG. 10B is a graphical representation of the induction ratios (ON/OFF) for the data presented in FIG. 12A. As was reported for the cTA system, the magnitude of reporter gene expression for the regulated rcTA-induced system is greatly increased at 30° C. in comparison to that at 37° C., while the ON/OFF ratios are similar for both cTA and doubly regulated rcTA systems at either temperature. Thus the doubly regulated rcTA gene switch performs like the cTA system in CHO cells.

Example 19

Deposits of Biological Material at International Depository Authority

In support of this application three samples of biological material were deposited on Sep. 16, 2005 at the Canadian International Depository Authority in at the National Microbiology Laboratory, Health Canada, 1015 Arlington Street, Winnipeg, MB, Canada R3E 3R2. The deposits are merely intended to provide examples of the clones that may be generated in accordance with the present invention, and are in no way intended to be limiting. The details of the biological materials are as follows:

| Accession Number | Reference |
| --- | --- |
| 160905-01 | 293SF-CymR-rcTA #38 |
| 160905-02 | CHO rcTA/CymR 10-35 |
| 160905-03 | (3-4C) pAd CMV5-rcTA |

In specific embodiments the invention encompasses such biological materials, all cell lines and products derived therefrom. Copies of the receipts for the deposits have been filed in the instant application.

Example 20 rcTA Mutation 142Glu-142 Gly is Sufficient to Reverse DNA Binding Properties of CymR The three rcTA mutations (125Ala→125Val (mut1), 142Glu→142Gly (mut2) and 144Met→144Ile (mut3)) were corrected either one at a time or two at a time to determine the relative contribution of the three mutations to the reverse CymR phenotype. Table 2 provides a list of the plasmids used in this example to transfect 293-CR5-GFP cells with the transactivator sequences.

TABLE 2

Figure 11A:
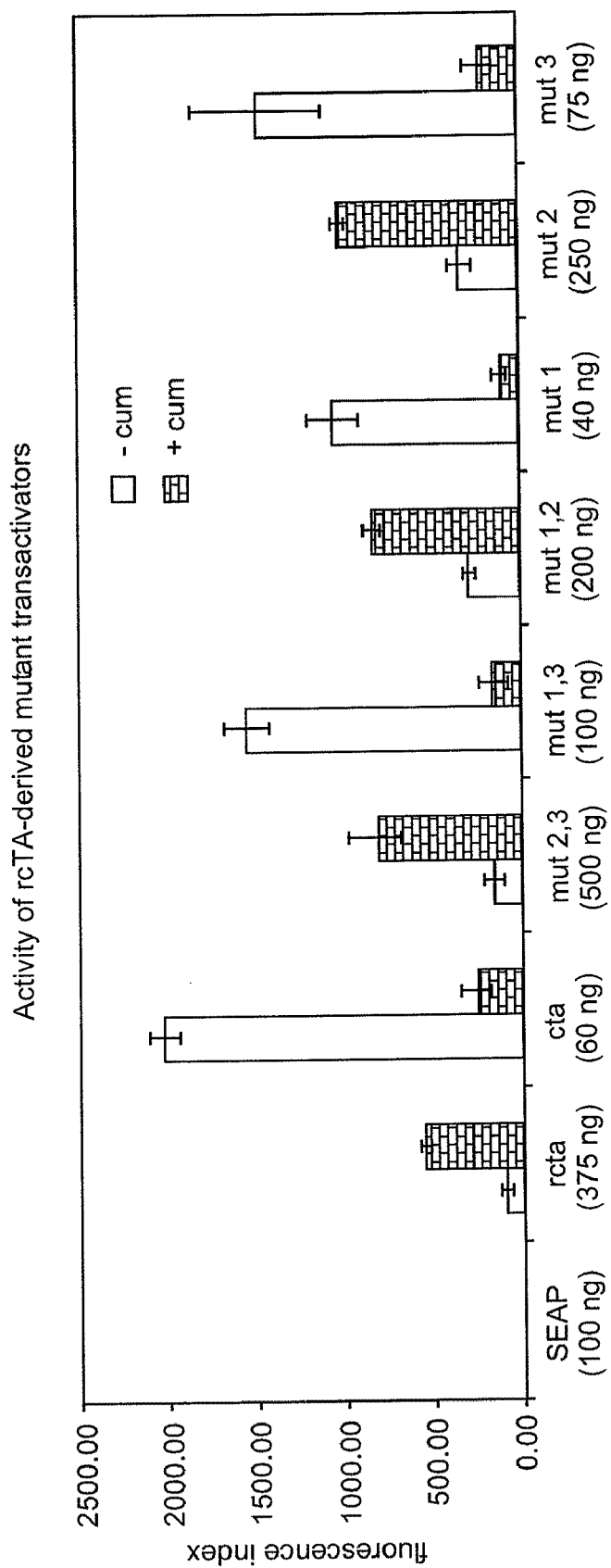
FIG. 11A: Activity of rcTA-derived mutant transactivators in 293-CR5-GFP cells in the presence (+cum) and absence (−cum) of cumate. Indicated quantities of each mutant were chosen to give rise to comparable levels of transactivator. The 142Glu→142Gly mutant is indicated as mut 2.
Figure 11B:
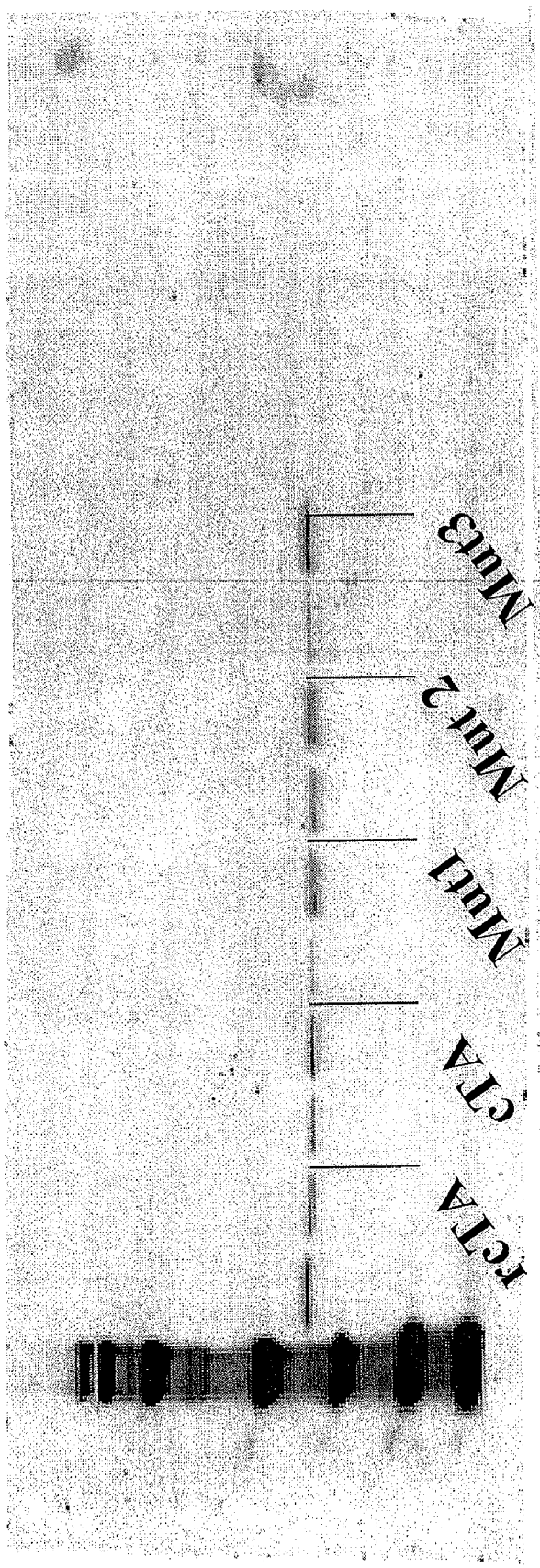
FIG. 11B: Western blot verifying expression levels of transactivators using acting as an internal control. The 142Glu→142Gly mutant is indicated as Mut 2.

| Mutation relative to CymR | Designation in FIGS. 11A and 11B | Name of plasmid |
| --- | --- | --- |
| none | cta | pAdK7CMVcTA |
| 125Val, 142Gly, 144Ile | rcta | pAdK7CMVrcTA3-4C |
| 125Val, 142Gly | mut1, 2 | pAdK7CMVcTA Mut1, 2 |
| 125Val, 144Ile | mut1, 3 | pAdK7CMVcTA Mut1, 3 |
| 142Gly, 144Ile | mut2, 3 | pAdK7CMVcTA Mut2, 3 |
| 125Val | mut1 | pAdK7CMVcTA Mut1 |
| 142Gly | mut2 | pAdK7CMVcTA Mut2 |
| 144Ile | mut3 | pAdK7CMVcTA Mut3 |

Plasmids pAdK7CMVrcTA3-4C and pAdK7CMVcTA containing the rcta and cta transactivator sequences, respectively, were constructed as previously described. Plasmids encoding the other transactivators listed in Table 2 were constructed as follows.
pAdK7CMVcTA Mut1,2

A first DNA strand (DNA#1) was created by digesting pAdK7CMVcTA Mut1,2,N (containing mutation 1 and 2 from the rcta, and another mutation N) with EcoRI-EcoRV and retaining the fragment with the beginning of CymR (containing the mutation 1 and 2). All of the backbone and mutation N are not retained in this fragment. A second DNA strand (DNA#2) was created by digesting pAdK7CMVrcTA3-4C with EcoRI-EcoRV and retaining the end of CymR and backbone. DNA#1 and DNA#2 were then ligated to create pAdK7CMVcTA Mut1,2.
pAdK7CMVcTA Mut1,3

PCR was performed on pAdK7CMVrcTA3-4C to correct the mutation #2. A first PCR (PCR1) on pAdK7CMVrcTA3-4C was performed with primers:

```
rev-2-     (SEQ ID NO: 5, gtcgtcgaggatatatggcttgg)
wild-F
and

MutagR     (SEQ ID NO: 9, gtttttcgtacgcgcgcggctgtac).
```

A second PCR (PCR2) was performed on pAdK7CMVrcTA3-4C with primers:

```
rev-2-     (SEQ ID NO: 6, ccaagccatatatcctcgacgac)
wild-R
and

S-Ecoil    (SEQ ID NO: 10, tccactttgcctttctctcc).
```

A third PCR (PCR 3) was performed using PCR1+PCR2 with primers MutagR and S-Ecoil. Then, enter PCR 3 NotI-BglII digested into pAdK7CMVcTA NotI-BglII.

pAdK7CMVcTA Mut2,3

PCR was performed on pAdK7CMVrcTA3-4C to correct the mutation #1. A first PCR (PCR1) was performed on pAdK7CMVrcTA3-4C with primers:

```
rev-1-     (SEQ ID NO: 7, gggatccagcgttacgcgaggg)
wild-F
and

MutagR     (SEQ ID NO: 9, gtttttcgtacgcgcgcggctgtac).
```

A second PCR (PCR2) was performed on pAdK7CMVrcTA3-4C with primers:

```
rev-1-wild-R (SEQ ID NO: 8, ccctcgcgtaacgctggatccc)
and

S-Ecoil      (SEQ ID NO: 10, tccactttgcctttctctcc).
```

A third PCR (PCR 3) was performed using PCR1+PCR2 with primers MutagR and S-Ecoil. Then, enter PCR 3 NotI-BglII digested into pAdK7CMVcTA NotI-BglII.

pAdK7CMVcTA Mut1

PCR was performed on pAdK7CMVcTA Mut1,3 to keep the mutation #1 and correct the mutation #3. A first PCR (PCR1) was performed on pAdK7CMVcTA Mut1,3 with primers:

```
mut2,3      (SEQ ID NO: 12, ggtttgtcgtcgaggatatgtgg
correctedF  cttggtgttc)
and MutagN      (SEQ ID NO: 13, ggggagaaaggacaggcg).
```

A second PCR (PCR2) was performed on pAdK7CMVcTA Mut1,3 with primers:

```
mut2,3      (SEQ ID NO: 11, agaacaccaagccacatatcctc
correctedR  gacgacaaacc)
and CR5atgseqF  (SEQ ID NO: 14, gatctggccatacacttg).
```

A third PCR (PCR 3) was performed using PCR1+PCR2 with primers MutagN and CR5atgseqF. Then, enter PCR 3 NotI-BglII digested into pAdK7CMVcTA NotI-BglII.

pAdK7CMVcTA Mut2

A first DNA strand (DNA#1) was created by digesting pAdK7CMVcTA Mut2,N (containing mutation 2 from the rcta, and another mutation N) with EcoRI-EcoRV and keeping the fragment with the beginning of CymR (containing the mutation 2). All of the backbone and mutation N are not in this fragment. A second DNA strand (DNA#2) was creating by digesting pAdK7CMVrcTA3-4C with EcoRI-EcoRV and keeping the fragment with the end of cymR and the backbone. Then DNA#1 and DNA#2 were ligated to create pAdK7CMVcTA Mut2.

pAdK7CMVcTA Mut3

A first DNA strand (DNA#1) was created by digesting pAdK7CMVcTA Mut3,N (containing mutation 3 from the rcta, and another mutation N) with EcoRI-EcoRV and keeping the fragment with the beginning of CymR (containing the mutation 3). All of the backbone and mutation N are not in this fragment. A second DNA strand (DNA#2) was created by digesting pAdK7CMVrcTA3-4C with EcoRI-EcoRV and keeping the fragment with the end of CymR and the backbone. Then, DNA#1 and DNA#2 were ligated to create pAdK7CMVcTA Mut3.

Plasmids that were created as described above were transfected into 293-CR5-GFP cells as previously described in quantities giving rise to comparable levels of transactivator. Activity of the transactivators was compared by measuring GFP levels. Co-transfected pcDNA-SEAP was used as an internal control (GFP/SEAP) and GFP levels were measured in the presence and absence of cumate. FIG. 11A provides the results, where DNA quantities transfected into the cells are given below each transactivator.

As is clear from FIG. 11A, when the 142Gly mutation is present (i.e. in rcta, mut2,3, mut1,2 and mut2) activity in the presence of cumate is increased over cta. In all cases where the 142Gly mutation is absent, activity is decreased in comparison to cta. Expression levels of the transactivators were verified by Western analysis (FIG. 11B), with actin used as internal control.

Whilst the invention has been described with reference to specific embodiments of the CymR variants, rcTA polypeptides, corresponding recombinant DNAs and expression systems of the present invention, a person of skill in the art would recognize that other CymR variants, rcTA polypeptides, corresponding recombinant DNAs and expression systems that have not been specifically described would nonetheless lie within the spirit of the invention. It is intended to encompass all such embodiments within the scope of the appended claims.

REFERENCES

1. Urlinger S, Baron U, Thellmann M, Hasan M T, Bujard H, Hillen W. Exploring the sequence space for tetracycline-dependent transcriptional activators: novel mutations yield expanded range and sensitivity. *Proc Natl Acad Sci USA*. 2000, 5; 97(14): 7963-8.
3A. Eaton R W. p-Cumate catabolic pathway in *Pseudomonas putida* F1: cloning and characterization of DNA carrying the cmt operon. *J Bacteriol*. 1996, 178(5): 1351-62.
3B. Eaton R W. p-Cymene catabolic pathway in *Pseudomonas putida* F1: cloning and characterization of DNA encoding conversion of p-cymene to p-cumate. *J Bacteriol*. 1997, 179(10): 3171-80.
4. Elahi S M, Oualikene W, Naghdi L, O'Connor-McCourt M, Massie B. Adenovirus-based libraries: efficient generation of recombinant adenoviruses by positive selection with the adenovirus protease. *Gene Ther*. 2002, 9(18): 1238-46.
5. Massie B et al. New adenovirus vectors for protein production and gene transfer. *Cytotechnology* 1998, 28: 53-64.

6. Chirumamilla R R, Muralidhar R, Marchant R, Nigam P. Improving the quality of industrially important enzymes by directed evolution. *Mol Cell Biochem.* 2001, 224(1-2): 159-68.
7. Oualikene W, Lamoureux L, Weber J M, Massie B. Protease-deleted adenovirus vectors and complementing cell lines: potential applications of single-round replication mutants for vaccination and gene therapy. *Hum Gene Ther.* 2000, 11(9): 1341-53.
8. Miescher S, Zahn-Zabal M, De Jesus M, Moudry R, Fisch I, Vogel M, Kobr M, Imboden M A, Kragten E, Bichler J, Mermod N, Stadler B M, Amstutz H, Wurm F. CHO expression of a novel human recombinant IgG1 anti-RhD antibody isolated by phage display. *Br J Haematol.* 2000, 111(1):157-66.
9. Haldankar R, Kopchick J J, Ridgway D. Stable production of a human growth hormone antagonist from CHO cells adapted to serum-free suspension culture. *Biotechnol Prog.* 1999, 15(3):336-46.
10. Massie B, Couture F, Lamoureux L, Mosser D D, Guilbault C, Jolicoeur P, Belanger F, Langelier Y. Inducible overexpression of a toxic protein by an adenovirus vector with a tetracycline-regulatable expression cassette. *J Virol.* 1998; 72(3): 2289-96.
11. Côté, J., Kamen, A, and Massie, B. Serum-free production of recombinant proteins and adenoviral vectors (filed on November 1998). U.S. patent issued September 2000.
12. Saez E, Nelson M C, Eshelman B, Banayo E, Koder A, Cho G J, Evans R M: Identification of ligands and coligands for the ecdysone-regulated gene switch. *Proc Natl Acad Sci USA* 2000, 97(26):14512-14517.
13. Neddermann P, Gargioli C, Muraglia E, Sambucini S, Bonelli F, De Francesco R, Cortese R: A novel, inducible, eukaryotic gene expression system based on the quorum-sensing transcription factor TraR. EMBO Rep 2003, 4(2): 159-165.
14. Zhao H F, Boyd J, Jolicoeur N, Shen S H: A coumermycin/novobiocin-regulated gene expression system. Hum Gene Ther 2003, 14(17):1619-1629.
15. Tascou S, Sorensen T K, Glenat V, Wang M, Lakich M M, Darteil R, Vigne E, Thuillier V: Stringent rosiglitazone-dependent gene switch in muscle cells without effect on myogenic differentiation. Mol Ther 2004, 9(5):637-649.
16. Weber W, Rimann M, Spielmann M, Keller B, Daoud-El Baba M, Aubel D, Weber C C, Fussenegger M: Gas-inducible transgene expression in mammalian cells and mice. Nat Biotechnol 2004, 22(11):1440-1444.
17. Fussenegger M, Morris R P, Fux C, Rimann M, Von Stockar B, Thompson C J, Bailey J E: Streptogramin-based gene regulation systems for mammalian cells. Nat Biotechnol 2000, 18:1203-1208.
18. Weber W, Fux C, Daoud-el Baba M, Keller B, Weber C C, Kramer B P, Heinzen C, Aubel D, Bailey J E, Fussenegger M: Macrolide-based transgene control in mammalian cells and mice. Nat Biotechnol 2002, 20(9):901-907.
19. United States patent publication 2004/0205834

Or

Mullick A, Warren R, Koutroumanis M, Guilbaut C, Malenfant F, Xu, Y, Jaramillo M, Caron A. W, Bourget, L., Lamoureux L, Jabbour N, Brousseau, S., O'Connor-McCourt M and Massie B. (2005). The cumate gene-switch: a system for inducible expression in mammalian cells. Submitted to BMC-Biotech 20. Elahi S M, Oualikene W, Naghdi L, O'Connor-McCourt M, Massie B. Adenovirus-based libraries: efficient generation of recombinant adenoviruses by positive selection with the adenovirus protease. *Gene Ther.* 2002, 9(18): 1238-46.

Or

Elhai, S. M., Oualikene, W, and Massie, B. Adenovirus-based libraries: efficient generation of recombinant adenoviruses by positive selection with the adenovirus protease. (CIP filed April 2001)

21. Fux C, Moser S, Schlatter S, Rimann M, Bailey J E, Fussenegger M. Streptogramin- and tetracycline-responsive dual regulated expression of p27 (Kip 1) sense and antisense enables positive and negative growth control of Chinese hamster ovary cells. Nucleic Acids Res. 2001 Feb. 15; 29(4)).

---

The invention claimed is:

1. An isolated polynucleotide encoding an isolated variant polypeptide of a cumate repressor protein (CymR), wherein the variant polypeptide comprises an amino acid sequence that has at least 95% identity to the amino acid sequence of SEQ ID NO: 2, wherein the amino acid sequence of the variant polypeptide has Gly at the position corresponding to amino acid 142 of SEQ ID NO: 2, and wherein the variant polypeptide has a higher affinity for a CymR response element in the presence of cumate relative to wild-type *Pseudomonas putida* CymR protein.

2. A polynucleotide construct comprising the isolated polynucleotide of claim 1, in operable association with a promoter sequence suitable for causing expression of said isolated polynucleotide to generate said variant polypeptide when a host cell is transformed or transfected with said construct.

3. The construct of claim 2, further comprising in operable association with said isolated polynucleotide, at least one CymR response element, whereby expression of said isolated polynucleotide in the host cell to generate said variant polypeptide can be regulated at least in part through binding of CymR to said response element.

4. An isolated eukaryotic host cell transfected with the construct of claim 2.

5. The eukaryotic host cell of claim 4, wherein said eukaryotic cell is a mammalian cell.

6. A method for producing a recombinant protein in the eukaryotic host cell of claim 4, the method comprising the steps of:
   (a) transfecting the eukaryotic host cell with a second construct comprising:
      (i) a promoter sequence;
      (ii) at least one CymR response element; and
      (iii) an open reading frame encoding said recombinant protein in operable association with the promoter sequence of (i), and said at least one CymR response element of (ii); and
   (b) introducing an effector molecule that regulates CymR-mediated expression into the transfected eukaryotic host cell of step (a) to induce the expression of said open reading frame thereby generating said recombinant protein,
wherein said effector molecule is cumate, dimethyl-p-aminobenzoic acid (DM PABA), trimethylcumate, ethylbenzoate, 3,4-dimethylbenzoate, 4-ethylbenzoate, 4-t-butylbenzoate, 4-phenylbenzoate, 4-benzylbenzoate, 4-ethoxybenzoate, 4-propyloxybenzoate, 4-n-butyloxybenzoate, 4-chlorobenzoate, 4-bromobenzoate, 4-iodobenzoate, 4-bromomethylbenzoate, 3,4-dichlorobenzoate, 4-trifluoromethylbenzoate, 4-ethyl-m-xylene, 4-vinyltoluene, 4-n-propyltoluene, 4-allyltoluene, 4-fluoro-p-toluate, 3-chloro-p-toluate, 4-bromo-m-toluate or salts thereof.

7. The method of claim 6, wherein said promoter sequence of (i) is selected from the group consisting of cytomegalovirus (CMV), vasoactive intestinal peptide (VIP), thymidine kinase (tk), heat shock protein (HSP), major late promoter (MLP) and mouse mammary tumour virus (MMTV) promoters.

8. The method of claim 6, wherein said variant polypeptide is expressed in the eukaryotic host cell, thereby to facilitate transactivation and expression of said second construct in response to the presence of said effector molecule, thereby causing expression of said recombinant protein.

9. The isolated polynucleotide of claim 1, wherein the encoded variant polypeptide has Ala at the position corresponding to amino acid 125 of SEQ ID NO: 2, has Met at the position corresponding to amino acid 144 of SEQ ID NO: 2, or has Ala at the position corresponding to amino acid 125 of SEQ ID NO: 2 and has Met at the position corresponding to amino acid 144 of SEQ ID NO: 2.

10. The isolated polynucleotide of claim 1, wherein the encoded variant polypeptide is a fusion polypeptide further comprising a transactivation domain.

11. The construct of claim 2, wherein the encoded variant polypeptide has Ala at the position corresponding to amino acid 125 of SEQ ID NO: 2, has Met at the position corresponding to amino acid 144 of SEQ ID NO: 2, or has Ala at the position corresponding to amino acid 125 of SEQ ID NO: 2 and Met at the position corresponding to amino acid 144 of SEQ ID NO: 2.

12. The construct of claim 11, wherein the encoded variant polypeptide is a fusion polypeptide further comprising a transactivation domain.

13. The eukaryotic host cell of claim 4, wherein the encoded variant polypeptide has Ala at the position corresponding to amino acid 125 of SEQ ID NO: 2, has Met at the position corresponding to amino acid 144 of SEQ ID NO: 2, or has Ala at the position corresponding to amino acid 125 of SEQ ID NO: 2 and Met at the position corresponding to amino acid 144 of SEQ ID NO: 2.

14. The eukaryotic host cell of claim 13, wherein the encoded variant polypeptide is a fusion polypeptide further comprising a transactivation domain.

15. The method of claim 6, wherein the encoded variant polypeptide has Ala at the position corresponding to amino acid 125 of SEQ ID NO: 2, has Met at the position corresponding to amino acid 144 of SEQ ID NO: 2, or has Ala at the position corresponding to amino acid 125 of SEQ ID NO: 2 and Met at the position corresponding to amino acid 144 of SEQ ID NO: 2.

16. The method of claim 6, wherein the encoded variant polypeptide is a fusion polypeptide further comprising a transactivation domain.

* * * * *